(12) United States Patent
Mercola et al.

(10) Patent No.: US 10,001,470 B2
(45) Date of Patent: Jun. 19, 2018

(54) METHOD, SYSTEM AND COMPOSITION FOR OPTICALLY INDUCING CARDIOMYOCYTE CONTRACTION

(75) Inventors: Mark Mercola, Rancho Santa Fe, CA (US); Fabio Cerignoli, San Diego, CA (US); Jeffrey Price, Rancho Santa Fe, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 33 days.

(21) Appl. No.: 12/960,313

(22) Filed: Dec. 3, 2010

(65) Prior Publication Data

US 2011/0318775 A1    Dec. 29, 2011

Related U.S. Application Data

(60) Provisional application No. 61/266,920, filed on Dec. 4, 2009.

(51) Int. Cl.
| | | |
|---|---|---|
| *C12Q 1/18* | (2006.01) | |
| *C12N 13/00* | (2006.01) | |
| *C12M 1/42* | (2006.01) | |
| *G01N 33/50* | (2006.01) | |

(52) U.S. Cl.
CPC ... *G01N 33/5061* (2013.01); *G01N 2333/705* (2013.01); *G01N 2333/726* (2013.01)

(58) Field of Classification Search
None
See application file for complete search history.

(56) References Cited

U.S. PATENT DOCUMENTS

| | | |
|---|---|---|
| 2004/0137621 A1 | 7/2004 | Rosen et al. |
| 2009/0054954 A1 | 2/2009 | Foley et al. |
| 2009/0099038 A1* | 4/2009 | Deisseroth et al. ............ 506/12 |
| 2009/0257990 A1 | 10/2009 | Feld et al. |
| 2010/0190229 A1* | 7/2010 | Zhang et al. ............. 435/173.1 |

FOREIGN PATENT DOCUMENTS

| | | | |
|---|---|---|---|
| WO | WO 2004057333 A1 * | 7/2004 | |
| WO | WO 2009/025819 A1 | 2/2009 | |
| WO | WO 2009/062107 A1 | 5/2009 | |

OTHER PUBLICATIONS

Valiunas, V; "Coupling an HCN2-expressing cell to a myocyte creates a two-cell pacing unit" The Journal of Physiology, 587, 5211-5226, 2009.*
Tanaka, Toshiaki; et al; "Stimulation of Intercellular Communication of Poor-Communicating Cells by Gap-Junction-Competent Cells Enhances the HSV-TK_GCV Bystander Effect In Vitro" International Journal of Cancer, 91, 538-542, 2001.*
Graeber, Sybilla HM; Husler, Dieter F; "Connexin Transfection Induces Invasive Properties in HeLa Cells" Experimental Cell Research, 243, 142-149, 1998.*
He, Jia-Qiang; et al; "Human embryonic stem cell-derived cardiomyocytes: drug discovery and safety pharmacology" Expert Opinions on Drug Delivery, 2, 739-753, 2007.*
Zhang et al., "Channelrhodopsin-2 and optical control of excitable cells", Nat. Methods., 3(10):785-92 (2006).
Supplementary European Search Report (ESR) from EP 10 83 5228.

* cited by examiner

Primary Examiner — David W Berke-Schlessel
(74) Attorney, Agent, or Firm — DLA Piper LLP (US)

(57) ABSTRACT

The present invention provides a method, system and composition for screening drug candidates for cardiotoxicity and for novel drugs that effect cardiomyocyte contractility and function. The invention provides an efficient and reliable screening assay to detect the effect of new and potential drug candidates on cardiomyocyte calcium flux, membrane depolarization, and/or the propagation of action potentials.

9 Claims, 13 Drawing Sheets

METHOD, SYSTEM AND COMPOSITION FOR OPTICALLY INDUCING CARDIOMYOCYTE CONTRACTION

CROSS REFERENCE TO RELATED APPLICATION

This application claims benefit of priority under 35 U.S.C. § 119(e) to U.S. Provisional Application No. 61/266,920 filed on Dec. 4, 2009, the disclosure of which is hereby incorporated by reference in its entirety for all purposes.

GRANT INFORMATION

This invention was made with government support under NIH/NHLBI Grant No. R42HL086076-01 awarded by the National Institutes of Health/National Heart, Lung, and Blood Institute. The government has certain rights in the invention.

BACKGROUND OF THE INVENTION

Field of the Invention

The present invention relates generally to screening assays and more particularly to a method, system and composition for screening agents that affect calcium flux, membrane depolarization, and/or the propagation of the action potential in cardiomyocytes.

Background Information

Cardiac arrhythmia and sudden cardiac death are two of the major topics for pharmaceutical industry both from therapeutic and toxicologic views. Atrial (AF) and ventricular (VF) fibrillation are the most common forms of arrhythmia and have major clinical implications. AF is the most prevalent in the population and its occurrence arises in the aging population, leading to the estimation that more than 15 millions of Americans will be affected by 2050. AF is also the major cause of stroke in elderly and is associated particularly with the more severe forms. The underlying cause of cardiac arrhythmia is the abnormal impulse formation and propagation in the heart resulting from altered (overactive or underactive) function of ion channels and exchangers that ultimately lead to an alteration of the heart beat rate and intensity of contraction. Therefore, arrhythmia undermines the process whereby electrical excitation leads to the muscular contraction that provides the pumping function of the heart.

A new generation of anti-arrhythmic drugs for example is under development to target channels that are specifically expressed in the atria, like Kv1.5 potassium channel that is responsible for the $I_{Kur}$ current. Abnormalities in intracellular $Ca^{2+}$ handling occur in a range of arrhythmogenic conditions, including congestive heart failure (CHF), ischemic heart disease, myocardial hypertrophy and inherited diseases such as catecholaminergic polymorphic ventricular tachycardia (CPVT). Calcium leak from the SR or attenuated calcium uptake are known to promote after-depolarizations that lead to atrial and ventricular fibrillation. Modulating the interaction between RyR2 receptor and the Calstabin 2 regulator is one of the approaches under evaluation to reduce $Ca^{2+}$ leak in patients with chronic AF.

Another target for future anti-arrhythmic drugs is the intracellular coupling machinery. Gap junctions are clusters of closely packed hemichannel subunits that connect adjacent cells to allow the passage of ions and small molecules end electrically coupling the nearby cardiomyocytes in the heart. Connexins 43, 40 and 45 are the most abundantly expressed in myocardium, where connexin 43 dominates working ventricular and atrial myocytes while connexin 40 is expressed in atrium and along with connexin 45 in conduction tissue. Changes in gap junction function and organization has been identified in several arrhythmia models and is known to affect the conduction velocity. Increasing gap-junctional coupling can favor anti-arrhythmia by improving cell-to-cell communication and thereby conduction velocity. Anti-arrhythmic peptides were first identified in 1980 and led to the identification of the stable analogue rotigaptide.

Another concern for cardiac arrhythmia is represented by new drugs that are under development or have been approved recently for marketing, when their effects in a large sample population have not been completely evaluated. In recent years several blockbuster drugs were withdrawn from the market or have undergone severe labeling restrictions due to safety issues. The widely popular non-sedating antihistamine Terfenadine (Seldane™), the gastric prokinetic Cisapride (Propulsid™) and the blockbuster anti-inflammatory Rofecoxib (Vioxx™) are examples of drugs removed from the market for causing polymorphic ventricular tachycardia (torsade de pointes or TdT) and sudden cardiac death. Cardiotoxicity is also a substantial problem in the field of anti-cancer drugs, as effective anti-neoplastic agents in the anthracycline class (e.g., doxorubicin) are cardiotoxic likely by interfering with cardiac metabolism. Thus, there is an ongoing effort to identify compounds that will be effective anti-tumor agents but not affect heart muscle cells, or to develop cardioprotective agents to be administered with the anthracycline-class compounds.

Drugs that have been withdrawn aftermarket are only the tip of the iceberg, although they are the most stunning examples, and it has been estimated that between 80% and 96% of the drugs under development fail the clinical trials, mainly for toxicity concerns. Withdrawal of medications from late stage development and from the market can cause severe financial losses, considering that the cost of a new drug development has been estimated in the range of up to $1.6 billion.

The main target of drug cardiotoxicity is the human homolog of *Drosophila*'s EAG gene (hERG), a $K^+$ channel with properties resembling those of the $I_{Kr}$ current. Blockade of the hERG channel is known to delay the repolarization current and induces a prolongation of the ventricular action potential and increases the possibility of early after-depolarization (EAD), resulting from reopening of L-type calcium channels during the late repolarization phase. Furthermore, a reduction in hERG current is known to have a greater effect on mid-myocardium relative to other regions of ventricular walls increasing the heterogeneity of tissue refractoriness. These two alterations increase the risk of arrhythmia and numerous evidences suggest that several non-cardiac drugs bind to hERG channels, increasing the risk of QT prolongation and torsades de pointes (TdT), a specific variety of ventricular tachycardia characterized by a distinctive twisting of the QRS complex around the baseline in the ECG and at high risk of degenerating into ventricular fibrillation and sudden death.

A remarkable feature of compounds that have been associated with high risk of TdT is their large diversity in both therapeutic action and chemical structure. Different from other channels, hERG has a large inner cavity size where the compounds tend to be trapped on closure of the activation gate. The inhibition is contingent upon channel gating;

suggesting that the channel needs to open for compound binding, with consequent relatively slow recovery after washout.

Despite the multiplicity of causes for arrhythmia (environmental, age, genetic background) and the fact that arrhythmia targets specific regions of the heart (AF vs. VF), with differences in impulse generation and propagation, there are only few anti-arrhythmic drugs with low selectivity and their use has decreased in the past years. This is mainly due to problems with the ability of the drugs to have a larger pro-arrhythmic effect in other regions of the heart. There is therefore a major unmet need for drugs that will control arrhythmia more safely and effectively.

SUMMARY OF THE INVENTION

The present invention is based in part on an improved system, composition and screening method for identification of cardiotoxic compounds and novel drugs that affect phenomena such as calcium flux, membrane depolarization, and/or the propagation of the action potential in cardiomyocytes.

Accordingly, in one embodiment, the present invention provides a cocultured cellular composition. The composition includes a cardiomyocyte; and a non-cardiomyocyte cell; wherein at least one non-cardiomyocyte cell includes a heterologous nucleic acid encoding a light sensitive protein, with the proviso that the cardiomyocyte does not include a light sensitive protein. In various aspects, at least one non-cardiomyocyte cell contains an endogenous connexin. In various aspects, at least one non-cardiomyocyte cell includes a heterologous nucleic acid encoding a connexin protein in addition to the light sensitive protein. In one aspect, the connexin protein can include any of Cx23, Cx25, Cx26, Cx29, Cx30, Cx30.2, Cx30.3, Cx31, Cx31.1, Cx31.9, Cx32, Cx33, Cx36, Cx37, Cx39, Cx40, Cx40.1, Cx43, Cx45, Cx46, Cx47, Cx50, Cx59, Cx62, or a combination thereof. In another aspect, the connexin is Cx42, Cx43, Cx45, or combination thereof. In one aspect, the light sensitive protein is an ion channel protein or a protein that activates a G-protein signaling cascade that activates an ion channel. In an additional aspect, the ion channel protein includes Channelrhodopsin1 (ChR1) or Channelrhodopsin2 (ChR2).

In one aspect, the non-cardiomyocyte cell is a HeLa cell, CHO cell, NIH/3T3 cell, HEK293 cell, or a combination thereof. In another aspect, the heterologous nucleic acid includes an inducible promoter. In another aspect, the culture composition of the invention includes a plurality of cardiomyocytes and non-cardiomyocyte cells connected via a plurality of gap junctions. In an additional aspect, the plurality of cardiomyocytes and non-cardiomyocyte cells are arranged as a monolayer. In various aspects, the ratio of cardiomyocytes to other non-cardiomyocyte cells expressing an exogenous light sensitive protein is greater than about 1:1, 2:1, 3:1, 4:1, 5:1, 10:1, 50:1, 100:1, 500:1 or 1000:1.

In one aspect, the non-cardiomyocyte cell includes a heterologous nucleic acid encoding a light sensitive protein, for example a Channelrhodopsin1 (ChR1) or Channelrhodopsin2 (ChR2), in combination with a connexin protein, for example Cx43. In various aspects, the composition includes a plurality of cardiomyocytes and non-cardiomyocyte cells expressing an exogenous light sensitive protein and/or a connexin protein connected via a plurality of gap junctions. The composition is typically arranged as a cocultured monolayer of cells.

In another embodiment, the invention provides a method of screening a drug candidate for cardiotoxicity. The method includes providing a cocultured sample including a cardiomyocyte and a non-cardiomyocyte cell; wherein at least one non-cardiomyocyte cell includes a heterologous nucleic acid encoding a light sensitive protein, and optionally at least one non-cardiomyocyte cell includes a connexin protein; contacting the sample with a drug candidate; optically activating the light sensitive protein producing an efflux of cations from the non-cardiomyocyte cell; and measuring the effect of the efflux of cations on the cardiomyocyte, thereby screening the drug candidate for cardiotoxicity. In various aspects, measuring the effect of the efflux of cations on the cardiomyocytes includes measuring cardiomyocyte action potential, cardiomyocyte intracellular calcium level, velocity of conduction, or a combination thereof. In one aspect, the sample is cocultured for at least 1, 2, 3, 4, or 5 days before contacting the sample with the drug candidate. In another aspect, the non-cardiomyocyte cell is stably transformed with the heterologous nucleotide.

In various aspects, at least one non-cardiomyocyte cell includes a heterologous nucleic acid encoding a connexin protein in addition to the light sensitive protein. In one aspect, the connexin protein can include any of Cx23, Cx25, Cx26, Cx29, Cx30, Cx30.2, Cx30.3, Cx31, Cx31.1, Cx31.9, Cx32, Cx33, Cx36, Cx37, Cx39, Cx40, Cx40.1, Cx43, Cx45, Cx46, Cx47, Cx50, Cx59, Cx62, or a combination thereof. In another aspect, the connexin is Cx42, Cx43, Cx45, or combination thereof. In one aspect, the light sensitive protein is an ion channel protein or a protein that activates a G-protein signaling cascade that activates an ion channel. In an additional aspect, the ion channel protein includes Channelrhodopsin1 (ChR1) or Channelrhodopsin2 (ChR2).

In one aspect, the non-cardiomyocyte cell is a HeLa cell, CHO cell, NIH/3T3 cell, HEK293 cell, or a combination thereof. In another aspect, the heterologous nucleic acid includes an inducible promoter. In another aspect, the cardiomyocyte and non-cardiomyocyte cell are connected via a plurality of gap junctions. In an additional aspect, the plurality of cardiomyocytes and non-cardiomyocyte cells are arranged as a monolayer. In various aspects, the ratio of cardiomyocytes to other non-cardiomyocyte cells expressing an exogenous light sensitive protein is greater than about 1:1, 2:1, 3:1, 4:1, 5:1, 10:1, 50:1, 100:1, 500:1 or 1000:1.

In another embodiment, the present invention provides a system for screening a drug candidate for cardiotoxicity. The system includes a coculture of cells including a cardiomyocyte and a non-cardiomyocyte cell; wherein at least one non-cardiomyocyte cell includes a heterologous nucleic acid encoding a light sensitive protein and optionally a connexin protein; an optical device to activate the light sensitive protein; a chemical delivery device for introducing the drug candidate to be screened; a sensor; a processor including executable code to process data received from the sensor; and memory for storing data received from the sensor. In one aspect, the system includes a voltage generator for delivering a voltage to the culture. In another aspect, the system includes a graphical user interface. In another aspect, the sensor may be an optical sensor, voltage sensor, ion sensor, or a combination thereof for measuring the effect of cation efflux on cardiomyocytes.

In another embodiment, the present invention provides a method of optically inducing cardiomyocyte contraction. The method includes providing a cocultured sample including a cardiomyocyte and a non-cardiomyocyte cell; wherein at least one non-cardiomyocyte cell includes a heterologous nucleic acid encoding a light sensitive protein, and optionally at least one non-cardiomyocyte cell includes a connexin protein; and optically activating the light sensitive protein producing an efflux of cations from the non-cardiomyocyte cell; thereby inducing contraction of the cardiomyocyte.

In various aspects, at least one non-cardiomyocyte cell includes a heterologous nucleic acid encoding a connexin protein in addition to the light sensitive protein. In one aspect, the connexin protein can include any of Cx23, Cx25, Cx26, Cx29, Cx30, Cx30.2, Cx30.3, Cx31, Cx31.1, Cx31.9, Cx32, Cx33, Cx36, Cx37, Cx39, Cx40, Cx40.1, Cx43, Cx45, Cx46, Cx47, Cx50, Cx59, Cx62, or a combination thereof. In another aspect, the connexin is Cx42, Cx43, Cx45, or combination thereof. In one aspect, the light sensitive protein is an ion channel protein or a protein that activates a G-protein signaling cascade that activates an ion channel. In an additional aspect, the ion channel protein includes Channelrhodopsin1 (ChR1) or Channelrhodopsin2 (ChR2).

In one aspect, the non-cardiomyocyte cell is a HeLa cell, CHO cell, NIH/3T3 cell, HEK293 cell, or a combination thereof. In another aspect, the heterologous nucleic acid includes an inducible promoter. In another aspect, the cardiomyocyte and non-cardiomyocyte cell are connected via a plurality of gap junctions. In an additional aspect, the plurality of cardiomyocytes and non-cardiomyocyte cells are arranged as a monolayer. In various aspects, the ratio of cardiomyocytes to other non-cardiomyocyte cells expressing an exogenous light sensitive protein is greater than about 1:1, 2:1, 3:1, 4:1, 5:1, 10:1, 50:1, 100:1, 500:1 or 1000:1.

In another embodiment, the present invention provides a method of screening for an agent that modulates cardiomyocytes to identify new arrhythmogenic drugs. The method includes providing a cocultured sample comprising a cardiomyocyte and a non-cardiomyocyte cell; wherein at least one non-cardiomyocyte cell includes a heterologous nucleic acid encoding a light sensitive protein, contacting the sample with a test agent; optically activating the light sensitive protein producing an efflux of cations from the non-cardiomyocyte cell; and identifying an effect of the efflux of cations on the cardiomyocyte, thereby identifying the agent as a modulator of cardiomyocytes. In various aspects, identifying an effect of the efflux of cations on the cardiomyocytes includes detecting an increase or decrease in one or more of cardiomyocyte action potential, cardiomyocyte intracellular calcium level, or velocity of conduction.

In various aspects, at least one non-cardiomyocyte cell includes a heterologous nucleic acid encoding a connexin protein in addition to the light sensitive protein. In one aspect, the connexin protein can include any of Cx23, Cx25, Cx26, Cx29, Cx30, Cx30.2, Cx30.3, Cx31, Cx31.1, Cx31.9, Cx32, Cx33, Cx36, Cx37, Cx39, Cx40, Cx40.1, Cx43, Cx45, Cx46, Cx47, Cx50, Cx59, Cx62, or a combination thereof. In another aspect, the connexin is Cx42, Cx43, Cx45, or combination thereof. In one aspect, the light sensitive protein is an ion channel protein or a protein that activates a G-protein signaling cascade that activates an ion channel. In an additional aspect, the ion channel protein includes Channelrhodopsin1 (ChR1) or Channelrhodopsin2 (ChR2).

In one aspect, the non-cardiomyocyte cell is a HeLa cell, CHO cell, NIH/3T3 cell, HEK293 cell, or a combination thereof. In another aspect, the heterologous nucleic acid includes an inducible promoter. In another aspect, the cardiomyocyte and non-cardiomyocyte cell are connected via a plurality of gap junctions. In an additional aspect, the plurality of cardiomyocytes and non-cardiomyocyte cells are arranged as a monolayer. In various aspects, the ratio of cardiomyocytes to other non-cardiomyocyte cells expressing an exogenous light sensitive protein is greater than about 1:1, 2:1, 3:1, 4:1, 5:1, 10:1, 50:1, 100:1, 500:1 or 1000:1.

In one aspect, the sample is cocultured for at least 1, 2, 3, 4, or 5 days before contacting the sample with the drug candidate. In another aspect, the non-cardiomyocyte cell is stably transformed with the heterologous nucleotide.

DETAILED DESCRIPTION OF THE INVENTION

The present invention is based in part on novel screening methods allowing for the detection of agents that are affect calcium flux, membrane depolarization, and/or the propagation of the action potential in cardiomyocytes. The present invention overcomes problems associated with conventional methodologies by utilizing light sensitive proteins which respond to optical stimulation to provide for excitation of cardiomyocytes to provide an innovative system, composition, and methodology.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a," "an," and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

Figure 1:
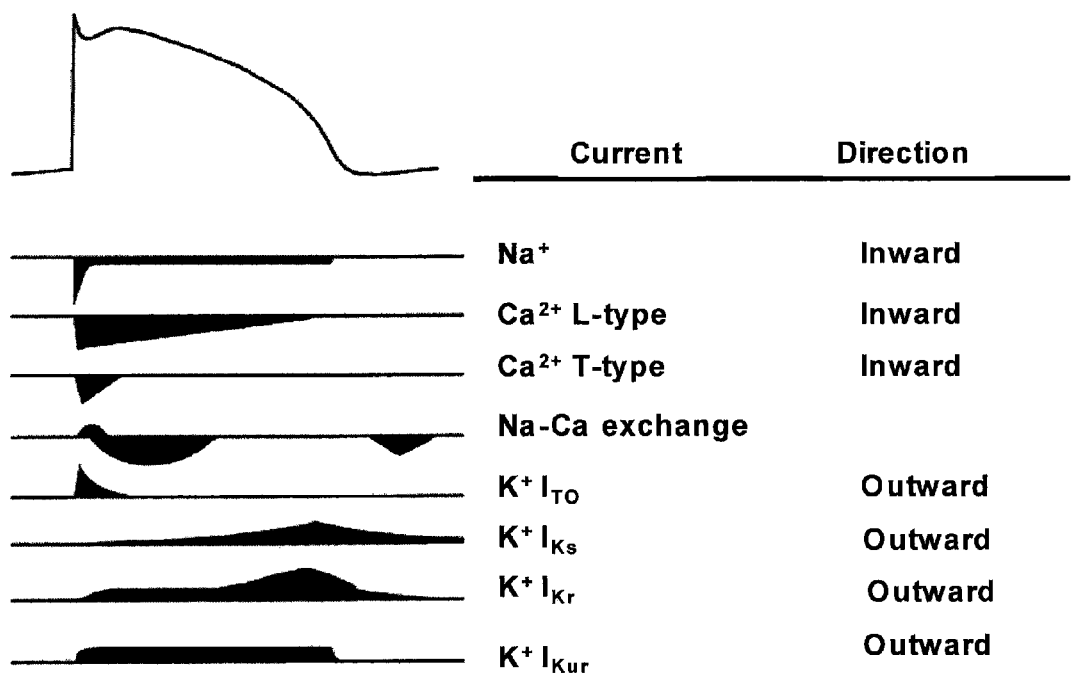
FIG. 1 is a pictorial representation of membrane ion conductance during the cardiac action potential.
Figure 2:
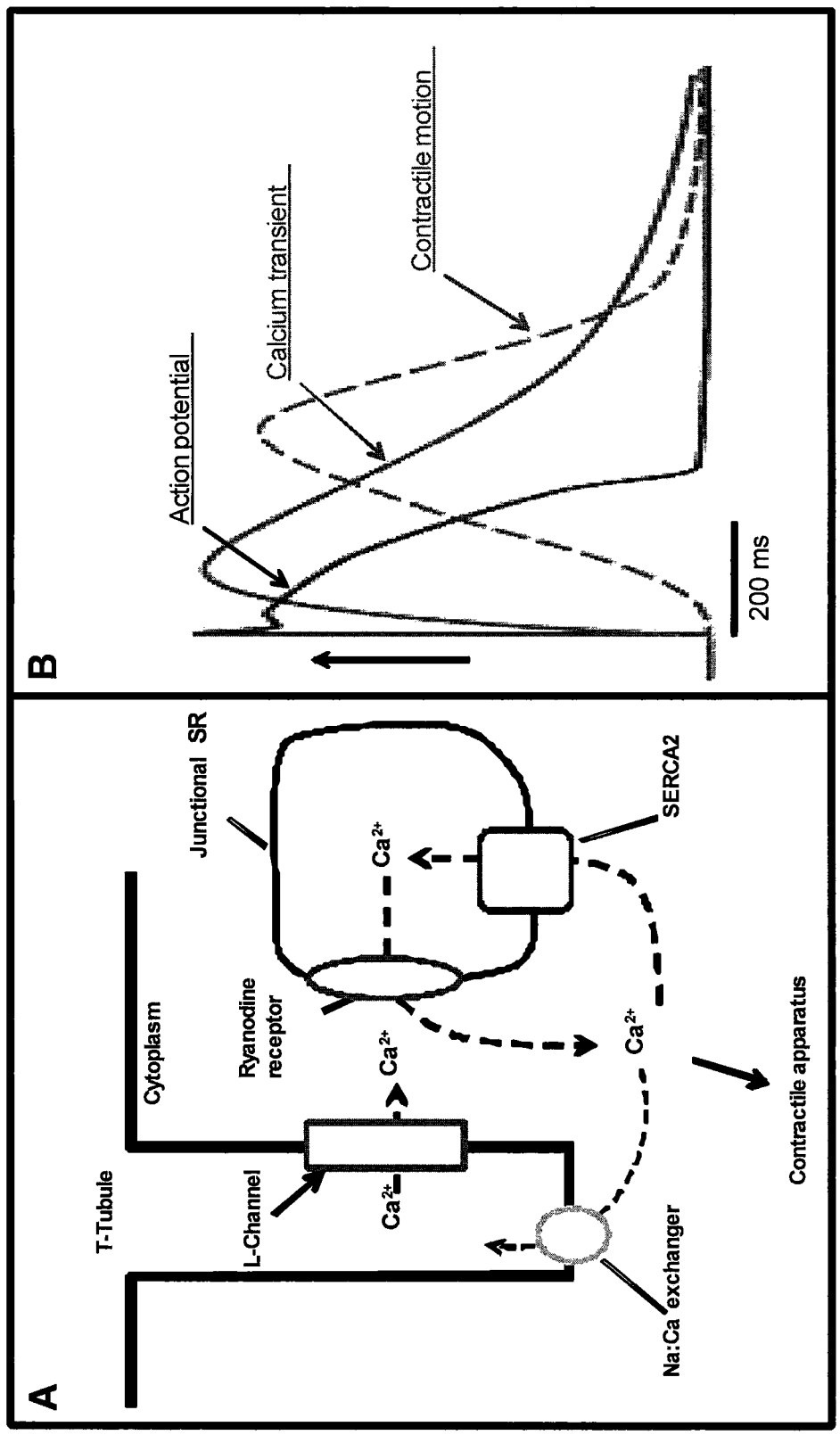
FIG. 2 is a pictorial representation of: A) calcium-induced calcium release from the SR and the role of SERCA2 to reuptake $Ca^{2+}$ into the SR; and B) cardiac action potential, calcium transient and myocyte contraction.

During the cardiac action potential, changes in ion channel conductance, and the consequently inward and outward ionic currents, confer the characteristic shape to the action potential. $Na^+$, $Ca^{2+}$ and $K^+$ are known to be the main ions involved in the process (FIG. 1). During the cardiac action potential, $Ca^{2+}$ entry, via voltage dependent L-type calcium channels, triggers the ryanodine receptor (RyR) opening and $Ca^{2+}$ release from the inside of the sarcoplasmic reticulum (SR). The increase of free intracellular calcium concentration $[Ca^{2+}]_i$ allows calcium binding to the myofilament protein troponin C, activating the contractile machinery. Finally, the action of several intracellular $Ca^{2+}$ transporters reduces $[Ca^{2+}]_i$, inducing myofilaments relaxation. SERCA2, an ATPase associated with the SR membrane, is the main protein involved in calcium reuptake by the SR. Additionally, a smaller amount of calcium is excluded from the cell by the Na:Ca exchanger, a calcium-transporting ATPase associated with the plasma membrane. FIG. 2A describes the calcium-induced calcium release from the SR and the role of SERCA2 to take $Ca^{2+}$ back into the SR. FIG. 2B shows the temporal gap between membrane depolarization, sarcoplasmic calcium release and contraction.

The pharmaceutical industry utilizes many existing approaches to assess cardiovascular risk. Many approaches are used in routine testing and have become standard over the past few years to assess the proarrhythmic potential of new drug candidates during the early phase of drug development or later in preclinical evaluation. Depending on throughput and cost, they are utilized at different stages of the product development process, but individually they do not represent a completely physiological assay. Physiological assays are essential since only a fraction of compounds that binds hERG channels in vitro for example induce arrhythmia and TdT in animal studies, reflecting the complexity of cardiac physiology. Moreover, effects on other targets could also cause arrhythmia or toxicity.

One approach to assess cardiovascular risk are high-throughput assays. Competitive binding of a test compound in comparison to a radiolabeled reference, rubidium efflux through potassium channels and measurement of cellular membrane potential with fluorescent dyes are relatively economical assays that can be adapted for high throughput use during the early phase of drug development. They rely on engineered tumor cell lines that undermine their physiological value.

Another approach is the traditional manual patch-clamp. Whole cell manual patch-clamp is the gold standard for determining the effects of drugs on the hERG channel. Various cells can be tested, including cells that naturally express hERG, such as isolated (typically rodent) ventricular cardiomyocytes, atrial cell lines or neuroblastoma cell lines. Alternatively, hERG can be expressed in other cells to simplify the measurement. This includes transient expression systems as the *Xenopus oocytes* or stably transfected mammalian cell lines, with Human Embryonal Kidney (HEK293) and Chinese Hamster Ovary (CHO) cells being the most commons. Automatic apparatus that can process tens of samples have been or are under development, but they are completely unreliable on cardiomyocytes (e.g., nanion SyncroPatch™ 96 apparatus).

Another approach utilizes the myocardial action potential. It is well accepted that even a potent blockade of the hERG channel does not necessarily lead to a QT prolongation. The reason why can be found in the fact that the effect of a compound on the action potential is the net result of the overall effects on the concerted activity of several ion channels. It is possible that the activity on a particular channel is masked by the effects on other competing channels. For this reason, measuring effects on the myocardial action potential provides a means to evaluate the physiological relevance of any activity. Myocardial action potentials are typically measured using electrodes in myocardial tissue such as purkinje fibers, papillary muscles, ventricular wedge preparation or the entire isolated heart. All these approaches are focused on measuring the action potential duration (APD), the time from a depolarization to a predefined percentage of repolarization. New systems are currently in development for whole cell automated patch-clamp. A critical step to the performance of the experiment is the formation of a tight, high resistance seal between the cell membrane and the hole in a planar chip. The formation of this seal remains the limiting factor, with success rates on the order of 50% per sample.

Another approach utilizes in vivo testing in rodents or other small animals. Heart rate, arterial blood pressure and electrocardiogram can be evaluated in small animals to determine the effects of pharmaceutical compounds. The parameters can be monitored continuously for 8-24 hours with small telemetry systems to ensure that all drug induced effects can be detected. While rodent species, especially rat, are preferably used for toxicity studies, their value for safety testing is less relevant due to the different panel of ion channels expression. The dog is a more valuable model and its use for both systemic hemodynamic and electrocardiogram is indispensable during preclinical development.

Physiological relevance and throughput are currently hard to coexist necessities: the higher the throughput of the test, the more it relies on artificial cellular models (e.g., tumor cell lines and exogenous expression of hERG channel). There is an unmet request of medium through-put physiological assays, relevant to cardiotoxicity and cardiac research in general, that can measure the activity of at least tens of compounds in a broad range of concentrations and replicates. Assays are required which are intended to measure intracellular ATP content, myofibril content, intracellular calcium flux and membrane potential in a broad spectrum of cardiac cells, included those derived from embryonic and induced pluripotent stem cells.

Current approaches for assessing calcium flux on cardiomyocytes include use of a Calcium Transient Image Cytometer (CTIC), an instrument able to electrically stimulate and record calcium flux on cardiomyocytes seeded on a 96-well dish. The instrument has been validated with compounds and siRNAs that affect action potential and calcium uptake. The instrument naturally finds several applications in basic biology and toxicity screening, however, there are limitations to the utilization of the instrument. One limitation is that the stimulation is provided by a couple of electrodes that are raised and lowered inside each well before and after the stimulation. This induces a delay of about 15 sec to the acquisition of every sample, while the autofocus/acquisition phase take 5-6 sec. Another limitation is that the electric current instantly stimulates all the cardiomyocytes in the well, preventing the measurements of important parameters like the conduction velocity. Another limitation is that the use of electric current for long time is somehow toxic to cells, affecting the ability to make multiple stimulation or measurement on the same sample. Another limitation is that the design of how the electrodes are placed inside the well renders it difficult to convert the instrument and assay to higher throughput (e.g., 384 or 1536-well plates).

The present invention is based on the seminal discovery of an assay method and system utilizing cell compositions of cocultured of cardiomyocytes and non-cardiomyocyte cells expressing exogenous light sensitive proteins, such as the light-gated ion channel Channelrhodopsin2 (ChR2), that allows for cation efflux from the non-cardiomyocyte cells upon optical stimulation resulting in electrical stimulation and contraction of the cardiomyocytes. Thus the present invention utilizes light sensitive proteins as a light trigger for cardiac excitation.

Accordingly, in one aspect, the present invention provides a method for optically inducing cardiomyocyte contraction. The method includes providing a cocultured sample including a cardiomyocyte and a non-cardiomyocyte cell expressing an exogenous light sensitive protein and optionally a connexin protein; and optically activating the light sensitive protein producing an efflux of cations from the cell to induce contraction of the cardiomyocyte.

As discussed herein, electrical stimulation of cardiomyocytes induces contraction of the cardiomyocyte resulting in propagation of an action potential. Such stimulation may be provided by increased levels of monovalent and bivalent cations. During propagation of the action potential, changes in ion channel conductance, and the consequently inward and outward ionic currents, confer the characteristic shape to the action potential. $Na^+$, $Ca^{2+}$ and $K^+$ are known to be the main ions involved in the process.

The close association of cardiomyocytes and the non-cardiomyocytes in culture allows the formation of gap junctions thus connecting the cardiomyocytes and non-cardiomyocyte cells. A gap junction is a specialized intercellular connection between cells that may directly connect the cytoplasm of two cells, which allows various molecules and ions to pass freely between cells. However, as provided in the present invention, the passing of ions may be controlled by optically controlling flow of ions using light sensitive proteins. Thus, controlled electrical stimulation and thus contraction of cardiomyocytes is provided by optically controlled light sensitive proteins expressed by non-cardiomyocytes closely associated via gap junction created by connexin proteins with the cardiomyocytes in the culture.

Thus in another aspect, the invention provides a cocultured cellular composition. The composition includes at least one cardiomyocyte; and at least one non-cardiomyocyte cell genetically engineered to express an exogenous light sensitive protein and optionally a connexin protein. The cellular composition is utilized as a component of an innovative system and method for performing cellular assays to determine cardiotoxicity of drug candidates.

A number of light sensitive proteins that may be utilized in the present invention. In one aspect, the light sensitive protein may be a light-gated ion channel protein, such as a channelopsin or channelrhodopsin. Channelrhodopsins (ChRs) are microbial type rhodopsins with an intrinsic light-gated cation conductance. In one embodiment, the photosensitive protein is from *C. reinhardtii*, which forms passive ion transport systems, e.g., Channelopsin1 (ChR1) and Channelopsin2 (ChR2). Channelrhodopsins are a sub-family of light-gated ion channels isolated from unicellular green algae *Chlamydomonas reinhardtii*, where they control movement in response to light. ChR2 has been utilized mainly in mammalian systems due to its faster time response and the ability to utilize Vitamin A, normally present in the mammalian environment, as prosthetic group. The channel is opened by blue light (maximum at 460 nm wave length) and it is permeable to monovalent and bivalent cations, such as $Li^+$, $Na^+$, $K^+$, $Ba^{2+}$, $Sr^+$ and $Ca^{2+}$, but not to $Mg^{2+}$. Under constant illumination ChR2 reaches the maximum of its conductivity in less than 1 ms and rapidly desensitizes, suggesting the existence of a reversible "inactive state".

ChR1 from *Chlamydomonas reinhardtii* is specific for protons, whereas ChR2 is a less selective cation channel, however both may be used in the present invention. Since the conductance of ChR2 is higher than that of ChR1, ChR2 is preferred. Additionally, terminally truncate versions of ChR2 are known in the art and suitable for use in the present invention. For example, C terminally truncated versions of ChR2, including ChR2 (1-315) is substantially as active as the full-length protein. Light activation of ChR2 may result in depolarizations of 10-25 mV within 10 ms, with repolarization occurring within 200 ms.

In another embodiment, the light sensitive channel protein may be derived from a protozoon, a bacterium or an archaebacterium. In one embodiment, the photosensitive ion channel protein is derived from fungi, such as *Neurospora crassa, Fusarium sporotrichioides* and *Leptosphaeria maculans*; or *Chytridiomyceten* such as, for example, *Allomyces reticulates*; or from ciliates, such as *Fabrea saliva* or *Paramecium bursaria*; or from Foraminifera, such as *Amphistegina radiata*.

In another embodiment, the light sensitive protein may be a protein that activates a G-protein signaling cascade that activates an ion channel. The sensitization of cells to light when photostimulation is applied results in an intracellular increase of second messengers, including $IP_3$ and/or calcium ions. By coupling photoactivation of rhodopsin to a G-protein alpha subunit other than the alpha subunit of $G_q$, one can elicit, through photostimulation, a response other than an increase in intracellular $IP_3$, $Ca^{2+}$, and DAG. For example, one may fuse rhodopsin to the alpha subunit of $G_s$ or $G_i$ instead of $G_q$. Moreover, some $G_i$ proteins can open ion channels directly by binding to them. To couple the pathways controlled by various G-protein subunits to rhodopsin activation, the alpha subunit of $G_q$ may be replaced with a chimeric subunit of a G protein.

As used herein, light sensitive proteins include variants of wild type proteins which retain their light sensitive characteristics and capable of leading to cation efflux up on optical stimulation. As such, one or more of the residues of a light sensitive protein can be altered to yield a variant protein, so long as the variant is light sensitive. For example, ChR2 may be substituted at one or more residues of the wild type sequence to result in a protein that is sensitive to light of a different wavelength or band relative to wild type. Some substitutions may be conservative. Conservative amino acid substitutions include, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitution also include groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. However, the invention also envisions variants with non-conservative substitutions.

To assist in forming gap junction between cardiomyocytes and non-cardiomyocytes cells expressing exogenous light sensitive proteins, the cell may further be genetically engineered to express a connexin protein. Connexins, also known as gap junction proteins, are a family of structurally-related transmembrane proteins that assemble to form vertebrate gap junctions. Each gap junction is composed of two hemichannels, or connexons, which are themselves each constructed out of six connexin molecules. Gap junctions are essential for many physiological processes, such as the coordinated depolarization of cardiac muscle. Suitable connexins for use in the present invention include Cx23, Cx25, Cx26, Cx29, Cx30, Cx30.2, Cx30.3, Cx31, Cx31.1, Cx31.9, Cx32, Cx33, Cx36, Cx37, Cx39, Cx40, Cx40.1, Cx43, Cx45, Cx46, Cx47, Cx50, Cx59, and Cx62. In an exemplary aspect, Cx42, Cx43, and/or Cx45 are utilized.

Various method are well known in the art for introducing heterologous nucleic acid into a cell to provide expression thereof. The non-cardiomyocytes may be generated using any suitable method known in the art to introduce the nucleic acid encoding an exogenous light sensitive protein and optionally a connexin protein into the non-cardiomyocyte to allow expression thereof. Typically a nucleic acid may be introduced as a vector construct incorporating the heterologous nucleic acid sequence and subsequently introduced into the host cell via a number of methods known in the art. Standard techniques for the construction of expression vectors suitable for use in the present invention are well-known to one of ordinary skill in the art and can be found in such publications such as Sambrook J, et al., "Molecular cloning: a laboratory manual," (3rd ed. Cold Spring Harbor Press, Cold Spring Harbor, N.Y. 2001), incorporated herein by reference as if set forth in its entirety. Introduction of the construct into the non-cardiomyocyte allows integration of the heterologous nucleic acid and expression thereof by the host.

Accordingly, transformed non-cardiomyocytes may be generated using a variety of well known techniques including both viral and non-viral mediated techniques. Gene delivery vectors within the scope of the invention include, but are not limited to, isolated nucleic acid, e.g., plasmid-based vectors which may be extrachromosomally maintained, and viral vectors, e.g., recombinant adenovirus, retrovirus, lentivirus, herpesvirus, poxvirus, papilloma virus, or adeno-associated virus, including viral and non-viral vectors which are present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes.

Non-viral mediated techniques include, for example, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion. Other methods of transfection include proprietary transfection reagents such as Lipofectamine™, Dojindo Hilymax™, Fugene™, jetPEI™, Effectene™ and DreamFect™. Alternatively viral-based gene transfer and expression vectors may be utilized which enable efficient and robust delivery of genetic material to most cell types, in vitro or in vivo. Viral-based constructs integrated into host DNA result in high expression levels.

In addition to a nucleic acid segment that encodes a light sensitive protein and/or connexin protein, the vectors may additionally include other components or functionalities that further modulate gene delivery and/or gene expression, or that otherwise provide beneficial properties to the targeted cells. Such other components include, for example, components that influence uptake of the vector by the cell; components that influence localization of the transferred gene within the cell after uptake; components that influence expression of the gene, such as transcriptional promoters, e.g., inducible and constitutive promoters and the like, and components that allow for identification, such as fluorescent markers or selection markers.

In various embodiments, the light sensitive protein and connexin protein may be on the same or different expression vectors. For example, the light sensitive protein may be included in one plasmid while the connexin protein may be included in a separate plasmid.

The term "peptide," "polypeptide," and "protein" are used interchangeably herein unless otherwise distinguished to refer to polymers of amino acids of any length. These terms also include proteins that are post-translationally modified through reactions that include glycosylation, acetylation and phosphorylation.

The terms "polynucleotide" and "oligonucleotide" also are used herein to refer to nucleic acid molecules. Although no specific distinction from each other or from "nucleic acid molecule" is intended by the use of these terms, the term "polynucleotide" is used generally in reference to a nucleic acid molecule that encodes a polypeptide, or a peptide portion thereof, whereas the term "oligonucleotide" is used generally in reference to a nucleotide sequence useful as a probe, a PCR primer, an antisense molecule, or the like. Of course, it will be recognized that an "oligonucleotide" also can encode a peptide. As such, the different terms are used primarily for convenience of discussion.

A polynucleotide or oligonucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template.

A nucleic acid is "operably linked" when it is placed into a functional relationship with another nucleic acid sequence. For example, DNA for a presequence or secretory leader is operably linked to DNA encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used for expression, as will be appreciated by those in the art. Numerous types of appropriate expression vectors, and suitable regulatory sequences are known in the art for a variety of host cells.

The cellular compositions of the present invention may be generated by coculture of cardiomyocytes with non-cardiomyocytes under conditions to allow for gap junctions to form between the different cells. Typically, cells will be seeded onto a suitable solid support, such as a multiwell plate and allowed to form a monolayers of cells ideal for assaying. Depending on the number of each type of cell, different cell patterns may be created to allowing for ideal detection of cardiomyocyte contraction phenomena. For example, growth in certain patterns as discussed further herein may be ideal for measurement of velocity of conduction. In various embodiments, the ratio of cardiomyocytes to non-cardiomyocyte cells is greater than about 1:1, 2:1, 3:1, 4:1, 5:1, 10:1, 50:1, 100:1, 500:1 or even 1000:1.

Cardiomyocytes for use in the present invention may be derived from a number of sources. As used herein, a myocyte, also referred to as a muscle cell, is the type of cell found in muscles which arise from myoblasts. Cardiac myocytes are a specialized form of myocyte which arise from myoblasts and are related to the heart. As used herein, a cardiomyocyte is synonymous with cardiac myocyte and are intended to include myoblast derived cells related to the heart, such as cells that are responsible for generating electrical impulses in cardiac tissue.

Cardiomyocytes suitable for use in the present invention may be derived from any suitable source, such as cardiac and atrial cells derived from a mammal. Such cardiomyocytes may be, for example, adult or pediatric cardiomyocytes derived from cardiac tissue, such as atrial tissue. Cardiomyocytes may also be derived from stem cells, such as pluripotent stem cells. As used herein, pluripotent cells include cells that have the potential to divide in vitro for an extended period of time (greater than one year) and have the unique ability to differentiate into cells derived from all three embryonic germ layers, including the endoderm, mesoderm and ectoderm. Further, suitable cardiomyocytes may be derived from a variety of animals, such as mammals, including for example humans, rodents (including mice, rats, hamsters and guinea pigs), cats, dogs, rabbits, farm animals including cows, horses, goats, sheep, pigs, primates (including monkeys, chimpanzees, orangutans and gorillas), and the like. In one embodiment, cardiomyocytes are derived from human embryonic stem cells.

While the methods and applications of the present invention are suitable for use with cells of various species, derivation of the cells for use with the present invention may also be species specific. Accordingly, coculture may be of cells that are species specific. For example, the cells for use in the present invention may include only human cells. For example, the cells may be human cardiomyocytes and other human cells. Likewise, the cells are from another species of animal.

Cardiomyocytes may be readily isolated by disaggregating an appropriate tissue, such as cardiac tissue which is to serve as the source of the cardiomyocytes. A variety of methods are known in the art, for example, the tissue or can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, hyaluronidase, DNase, pronase, and/or dispase etc. Mechanical disruption can also be accomplished by a number of methods including, but not limited to the use of grinders, blenders, sieves, homogenizers, pressure cells, or insonators to name but a few.

In various aspects, cardiomyocytes from Sprague Dawley (SD) neonatal rats may serve as the source of cardiomyocytes, specifically, neonatal rat ventricular myocytes (NRVMs). NRVMs provide an ideal model for studying cardiomyocytes contractility: a large number of cells can easily be isolated and, once seeded on a cell culture plate, they respond to electrical stimulation, generating calcium transients and contracting. Therefore, NRVMs are easy to obtain and the closest cellular model to human cardiomyocytes. Established protocols for isolation of cardiac cells from neonatal rat allow the isolation, from a single preparation of 10-12 animals, between 3 and $6 \times 10^7$ cells, a number large enough to cover 6-8 96 well-plates.

As discussed above, additional non-cardiomyocyte cells may be present in the culture with the cardiomyocytes which may or may not all express a light sensitive protein and/or connexin protein. These additional cells may have a number of beneficial effects, including, among others, supporting growth in culture, enhancing synthesis of growth factors, and promoting attachment of cells. Additional cell types include as non-limiting examples, other myocytes, such as smooth muscle cells and skeletal muscle cells, stromal cells, fibroblasts, and endothelial cells. Such cells may be inoculated onto the coculture along with the cardiomyocytes and grown using methods well established in the art.

A variety of cell types may be suitable for expressing exogenous proteins and coculture with cardiomyocytes, so long as the cells are capable of forming gap junctions with the cardiomyocytes. Such cells include, for example, myocytes, such as smooth and skeletal muscle cells, stromal cells, fibroblasts, endothelial cells, cancer cells, and the like. In one aspect, cells of cell lines derived from immortalized cancer cells are utilized to express ChR2 and are co-cultured with cardiomyocytes. Particularly suitable cells include, for example, HeLa cells. Other suitable cell lines include, for example, 293-T, NIH/3T3, 721, 9L, A2780, A2780ADR, A2780cis, A172, A20, A253, A431, A-549, ALC, B16, B35, BCP-1, BEAS-2B, bEnd.3, BHK-21, BR 293, BxPC3, C3H-10T1/2, C6/36, Cal-27, CHO, COR-L23, COR-L23/CPR, COR-L23/5010, COR-L23/R23, COS-7, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, Hepa1c1c7, HL-60, HMEC, HT-29, Jurkat, JY, K562, Ku812, KCL22, KG1, KYO1, LNCap, Ma-Mel 1, 2, 3 . . . 48, MC-38, MCF-10A, MDA-231, MDA-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-373, NALM-1, NW-145, OPCN/OPCT, Peer, PNT-1A/PNT 2, RenCa, RMA/RMAS, Saos-2, Sf-9, SkBr3, T2, T84, THP1, U373, U87, U937, VCaP, Vero, WM39, WT-49, X63, YAC-1 and YAR. In a specific instance, the cell line is derived from HeLa cells in which such cells are stably transformed and coexpress ChR2 and Cx43.

In addition to the light sensitive proteins discussed so far, non-cardiomyocyte cells that express additional specific voltage-gated ion channels may be used or generated. For example, cells that express additional calcium, sodium, and potassium channels may be used or created using the methods described herein. For example, cell lines using particular voltage-gated calcium channels, voltage-gated sodium (e.g., $Na_v1.1$ through $Na_v1.9$), potassium (e.g., Kv such as hERG, TASK1, Shaker, or KvLQT1), or chloride conducting channels/pumps (e.g., members of the CLC family of chloride channels) may be used.

In another aspect, the invention provides a method of screening a drug candidate for cardiotoxicity. The method includes providing a cocultured sample including a cardiomyocyte and a non-cardiomyocyte cell including a heterologous nucleic acid encoding a light sensitive protein and optionally a connexin protein; contacting sample with a drug candidate; optically activating the light sensitive protein producing an efflux of cations from the cell; and measuring the effect of the efflux of cations on the cardiomyocyte, thereby screening the drug candidate for cardiotoxicity.

As used herein, the terms "sample" and refers to a sample suitable for the methods provided by the present invention. The sample can be any sample that may be used such that efflux of cations from a cell expressing a light sensitive protein on a cardiomyocyte in close contact with the cell, e.g., cocultured, may be detected and measured. Accordingly, in one aspect, the sample is a coculture of cells including cardiomyocytes and cells expressing an exogenous light sensitive protein.

To determine cardiotoxicity or effect of calcium efflux, the effect of the drug or test agent on the normal electrical stimulation and contraction is analyzed. In various aspects, measuring the effect of the efflux of cations on the cardiomyocytes includes measuring cardiomyocyte action potential, cardiomyocyte intracellular calcium level, or velocity of conduction.

The electrical stimulation phenomena of the cardiomyocytes may be tracked and recorded for several days before the drug candidate is contacted with the cells so that a base line may be established. For example, the cellular composition may be cocultured for at least 1, 2, 3, 4, or 5 days before contacting the sample with the drug candidate.

A drug candidate or test agent is intended to include any type of molecule, for example, a polynucleotide, a peptide, a peptidomimetic, peptoids such as vinylogous peptoids, chemical compounds, such as organic molecules or small organic molecules, or the like, which may effect cardiomyocyte contraction. Drug candidates and agents encompass numerous chemical classes, though typically they are chemical compounds, such as an organic molecule, and often are small organic compounds (i.e., small molecules) having a molecular weight of more than 100 Daltons and less than about 2,500 Daltons. Drug candidates and agents comprise functional groups necessary for structural interaction with proteins, particularly hydrogen bonding, and typically include at least an amine, carbonyl, hydroxyl or carboxyl group, preferably at least two of the functional chemical groups. The drug candidates and agents may often comprise cyclical carbon or heterocyclic structures and/or aromatic or polyaromatic structures substituted with one or more of the above functional groups. Drug candidates and test agents are also found among biomolecules including peptides, saccharides, fatty acids, steroids, purines, pyrimidines, derivatives, structural analogs or combinations thereof.

Drug candidates or test agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In another aspect, the present invention provides a method of screening for an agent that modulates cardiomyocytes to identify new arrhythmogenic drugs. The method includes providing a cocultured sample comprising a cardiomyocyte and a non-cardiomyocyte cell including a heterologous nucleic acid encoding a light sensitive protein, contacting the sample with a test agent; optically activating the light sensitive protein producing an efflux of cations from the cell; and identifying an effect of the efflux of cations on the cardiomyocyte, thereby identifying the agent as a modulator of cardiomyocytes. In various aspects, identifying an effect of the efflux of cations on the cardiomyocytes includes detecting an increase or decrease in one or more of cardiomyocyte action potential, cardiomyocyte intracellular calcium level, or velocity of conduction.

As used herein, arrhythmogenic drugs are intended to include any drug producing or promoting arrhythmia, which is an irregularity in the force or rhythm of the heartbeat. As such, one of skill in the art would understand that agents that modulate the effects of electrical and/or cationic stimulation of cardiomyocytes via increases or decreases in one or more of cardiomyocyte action potential, cardiomyocyte intracellular calcium level, or velocity of conduction would be potential arrhythmogenic drugs.

The screening methods of the present invention may be performed on a number of platforms and utilize a variety of cell types. The methods of the present invention may be performed, for example using a cell based assay using the cellular composition described herein. As such, the method is particularly suited to be performed in a high-throughput fashion, (i.e., 96 or 384-well plate analysis; mechanical or robotic processing).

Accordingly, in another aspect, the present invention provides a system for screening a drug candidate for cardiotoxicity or for new arrhythmogenic drugs. The system includes a coculture of cells including a cardiomyocyte and a non-cardiomyocyte cell including a heterologous nucleic acid encoding a light sensitive protein and optionally a connexin protein as described herein; an optical device to activate the light sensitive protein; a chemical delivery device for introducing the drug candidate to be screened; a sensor; a processor including executable code to process data received from the sensor; and memory for storing data received from the sensor. The system may also include a graphical user interface for displaying data and analysis. Further, the system may include a voltage generator for delivering a voltage to the culture.

In various aspects, the sensor may be any type of sensor known in the art suitable for collecting data for to analyze the cardiotoxicity of a drug. For example, the sensor may be an optical sensor capable of, for example, providing imaging analysis of the sample. Such analysis may be fluorescent based microscopy or the like as is known in the art. The sensor may be a voltage sensor to measure electrical phenomena associated with the culture to track cardiomyocyte action potential or the like. The sensor may be an ion sensor for measuring ion activity intracellularly and extracellularly associated with the cell culture, for example, to analyze calcium transience.

The following examples are intended to illustrate but not limit the invention.

EXAMPLE 1

Automatic Calcium Fluorescence Acquisition and Quantization of Stimulated Cardiomyocytes A Calcium Transient Image Cytometer (CTIC) instrument and software have been developed at Vala Sciences to analyze calcium transient and other fluorescent read out in stimulated cardiomyocytes which is utilized in the Examples described herein. The instrument consists of a Nikon Eclipse™ microscope with a 20× objective, a Cohu 6612-3000 monochrome ½" digital/analog progressive scan camera (which operates at 30 or 60 Hz), a Pentium™ 4-based PC, and a 200 gigabyte external "firewire" hard drive.

Figure 3:
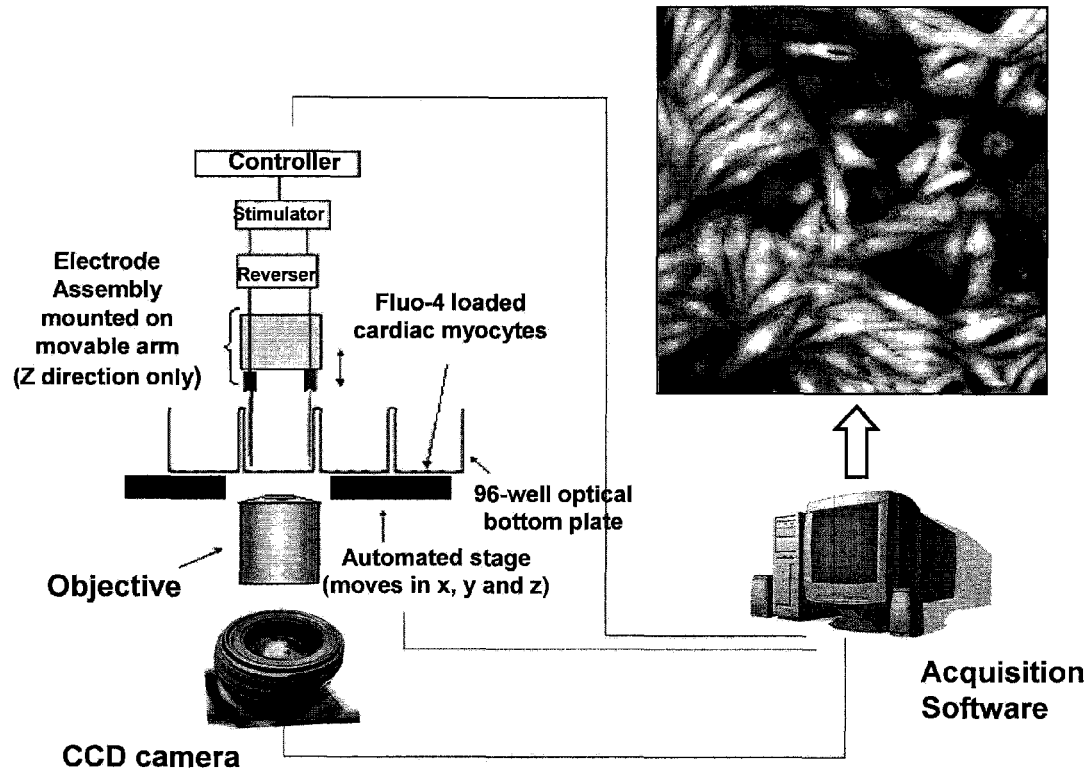
FIG. 3 is a pictorial representation of the electrode assembly of a Calcium Transient Image Cytometer (CTIC) for stimulating contractions of cardiomyocytes.
Figure 4A:
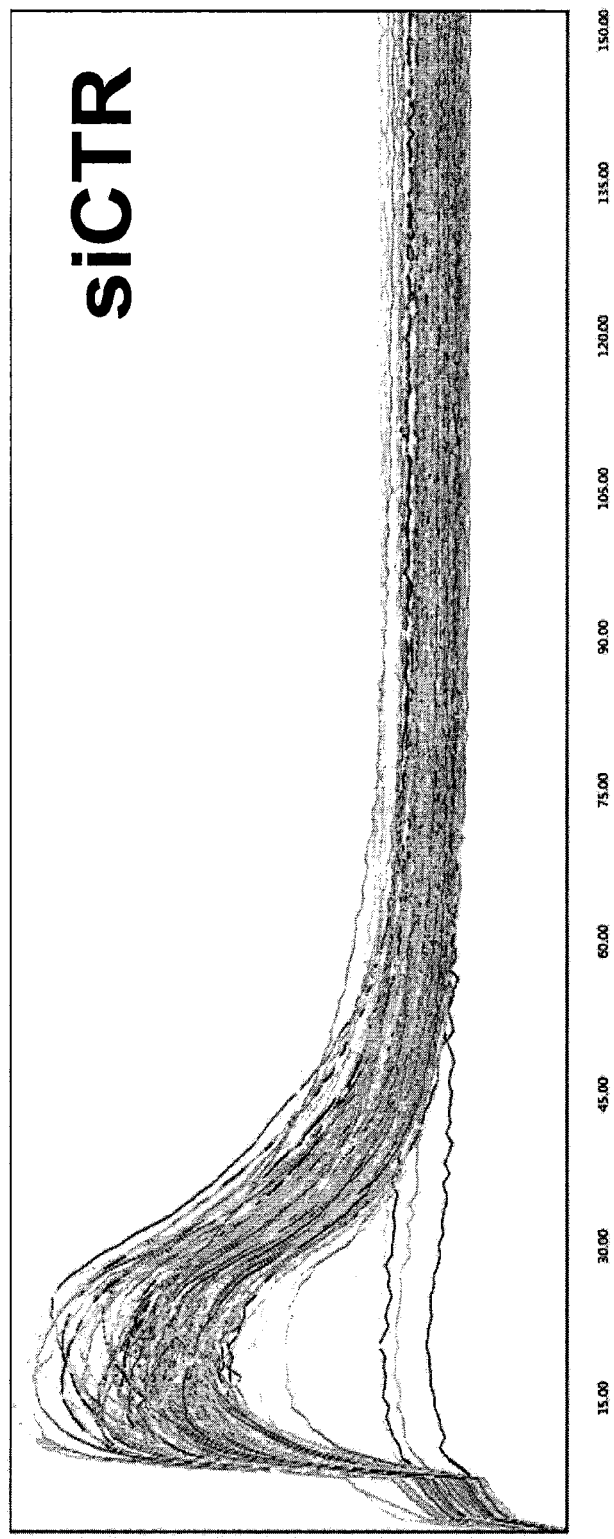
FIG. 4 is a graphical representations of single cell analysis of calcium flux in neonatal rat ventricular monocytes (NRVMs) transfected with siRNA against: A) CTR; B) SERCA2; and C) Phospholamban.
Figure 4B:
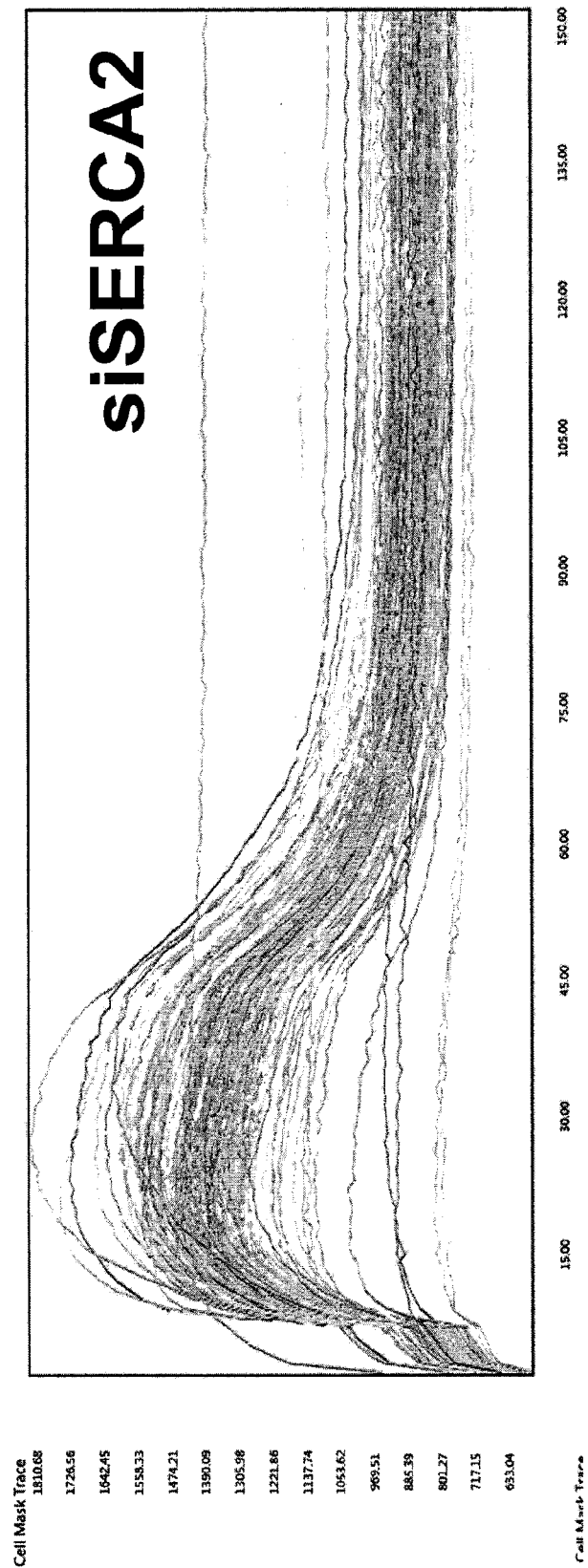
Figure 4C:
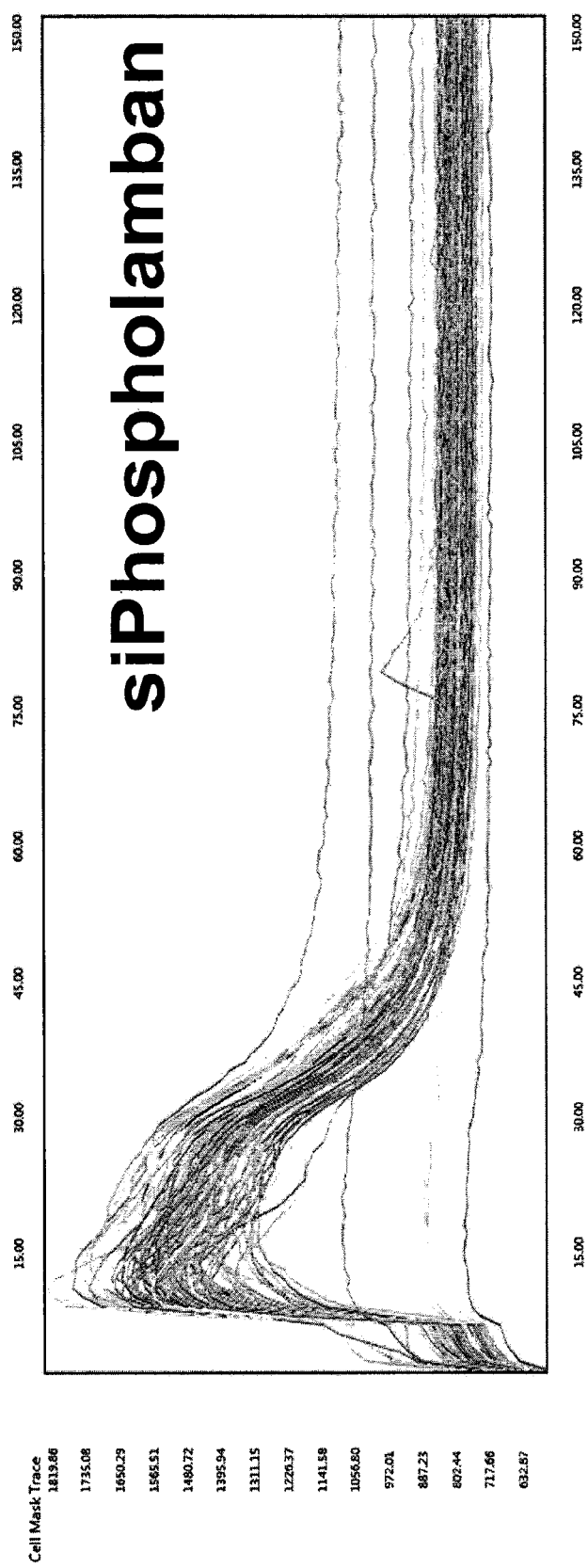

Platinum electrodes are mounted on a micromanipulator to stimulate cardiomyocytes cultured in a 96-well plate. The plate is placed, without a lid, on the stage of a robotic inverted microscope outfitted for fluorescence microscopy. The mechanical stage of the microscope moves to bring each well into position and the micromanipulator lowers to the pair of electrodes to bring them into contact with the culture medium of the well that is being analyzed. The voltage used to stimulate the cells is on the order of 20 to 30 volts, utilizing square wave pulses of 5 to 20 msec. A "polarity reverser" is included in the circuit to maintain electrode performance and effective stimulation of cardiac myocytes. FIG. 3 describes the prototype setting. After positioned on the well, the electrodes move to the "down" position, the instrument autofocuses on cells nuclei (blue channel), stimulates the cells (single stimulus or at 1 to 3 Hz for 3 to 10 seconds) and acquires the fluo-4 channel (green channel). Subsequently, the electrodes move to the "up" position and the instrument moves to another well, repeating the entire process. The time required to sample each well will range from 20 to 30 seconds, depending on the number of frames that are collected and the rate of stimulation.

The instrument is incorporated in a 37° C. chamber with $CO_2$ and $O_2$ percentage controllers, allowing the execution of experiment in approximate physiological conditions. The calcium analysis software, developed at Vala Sciences as a plug-in for Vala's CyteSeer High Content Analysis™ software, converts the fluo-4 and Hoechst 33342 fluorescence signals in a binary mask, to distinguish portions of the images corresponding to single cells. Then, comparing the images acquired during the stimulation, the software reports the calcium variation for the well or for every single cell and the average value for the well. Traces can be filtered to remove low responders or kinetics with specific characteristics.

In a typical experiment, cardiomyocytes are stimulated with a single pulse and several algorithms applied to the signal, normalizing to the value before the stimulation and to the maximum value reached, to obtain a curve that is comparable between cells. A number of kinetic parameters can be automatically derived either for the nuclear, cytoplasm or the whole cell compartments: The Full Width at Half Maximum (FWHM), which is the time required for progression from the 50% point on the upstroke to 50% point on the downstroke, $T_{Rise}$, which is the time from 50% point to 100% on the upstroke, and the $T_{Decay}$, which is the time period from 100% point to 50% point on the decay phase. Other values can be measured, including the time from 75% to 25% in the downstroke ($T_{75-25}$) and the value at a particular time. Values are measured for single cells in the well and as average of the well.

Figure 6A:
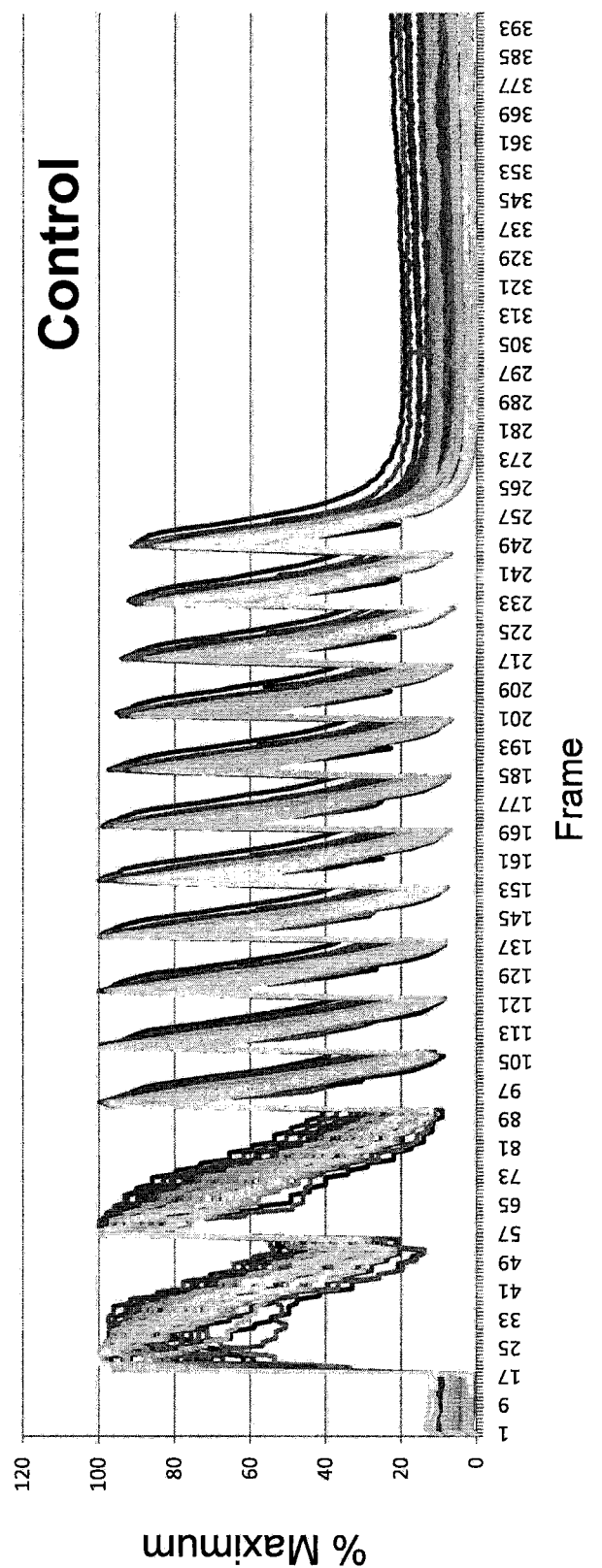
FIG. 6 is a graphical representation of single cell recording of continuous stimulation in NRVMs with: A) a control; and B) sparfloxacin.
Figure 6B:
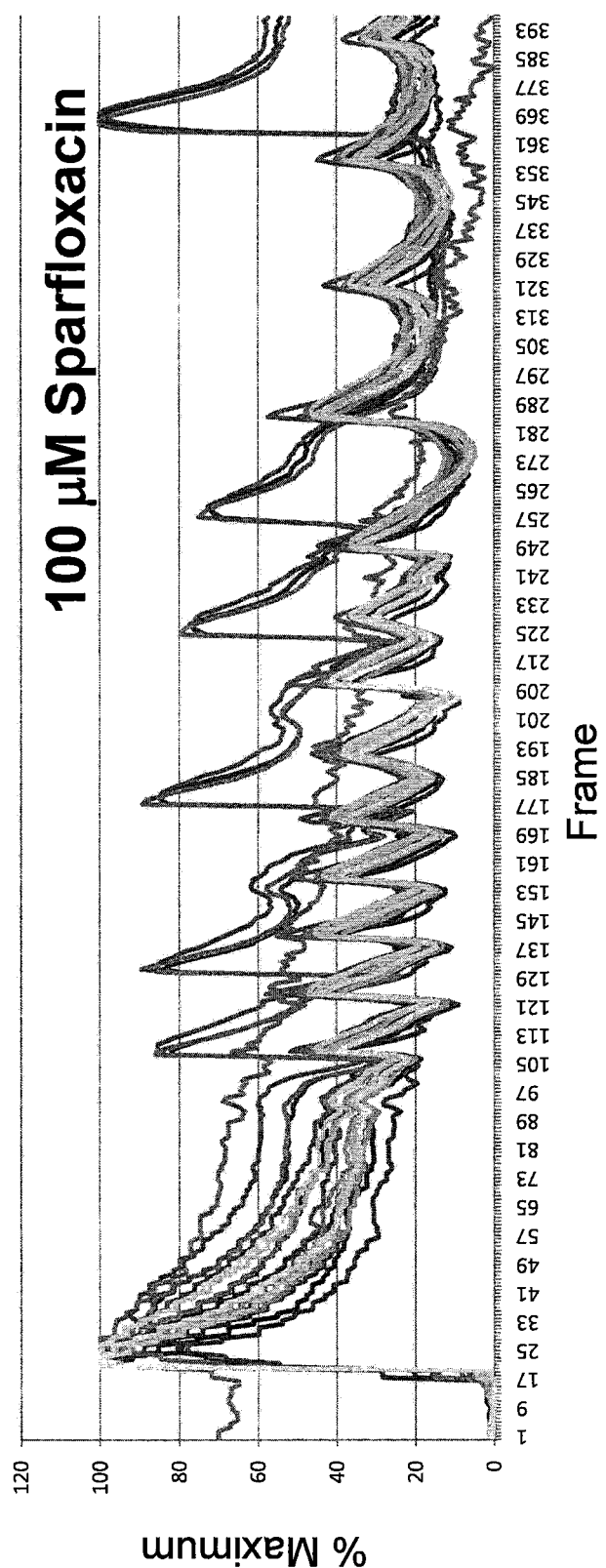

To demonstrate the ability of the instrument to quantify variations in intracellular calcium release, the instrument has been applied to Neonatal Rat Ventricular Myocytes (NRVMs) treated with compounds that alter the action potential or the calcium uptake machinery. In one set of experiments NRVMs have been transfected with siRNAs that target SERCA2, the pump responsible for the uptake of calcium inside the sarcoplasmic reticulum (SR), and phospholamban, a negative regulator of SERCA2. Two days after transfection the cells are fixed and stained to validate the interference and were stimulated and acquired by the CTIC (FIGS. 6A and 6B). FIGS. 6A and 6B show exemplary automatic calcium recordings from the same samples. It is clearly visible that opposite effects of the SERCA2 and phospholamban siRNAs. The images are acquired 2 days after transfection and the x axis show the number of frames while y axis show the average cell intensity. As expected, the reduction of the level of the SERCA2 pump slows down the uptake of $Ca^{2+}$, while the interference against phospholamban accelerates calcium sequestration, at least in the early phase of stimulation.

The CTIC and calcium recording have been validated also for toxicity-related analysis. In one set of experiments, NRVMs are treated with either sparfloxacin or cisapride. The first one is a fluoroquinolone antibiotic no longer available in the U.S., known to induce QT interval prolongation at high dosage. The second one is a serotonin 5-$HT_4$ receptor agonist, used to cure people with gastro esophageal reflux disease. The drug has been voluntarily removed from the U.S. market because of reports of causing long QT syndrome, Treatment with high dose of sparfloxacin (100 μM) during the stimulation clearly doubles the $T_{decay}$. The treatment with Cisapride (1 μM) not only induces an increase in $T_{decay}$, but causes early after depolarization (EAD), with new release of intracellular calcium before the previous event is complete. This is a clear hallmark of compounds that predispose to arrhythmia and torsades de pointes. The data are summarized in Table 1 and FIGS. 5A and 5B.

Table 1 shows $T_{decay}$ values for NRVMs treated with arrhythmogenic compounds. $T_{decay}$ is indicated for the average signal of three control wells and three compound treated wells. The mean, standard deviation (SD) and percent error is calculated for each group. The difference between the control and the compound groups is also indicated.

TABLE 1

$T_{decay}$ values.

| | | $T_{decay}$ | | |
|---|---|---|---|---|
| | | Mean (ms) | SD | Error (%) |
| Sparfloxacin | Control | 957 | 33 | 3.4 |
| | 100 µM | 1969 | 190 | 9.7 |
| Cisapride | Control | 935 | 38 | 4.1 |
| | 1 µM | 2145 | 114 | 5.3 |

| | Difference (ms) | Diff. (%) |
|---|---|---|
| CTR/Sparfloxacin | +1012 | +106 |
| CTR/Cisapride | +1210 | +129 |

Figure 5A:
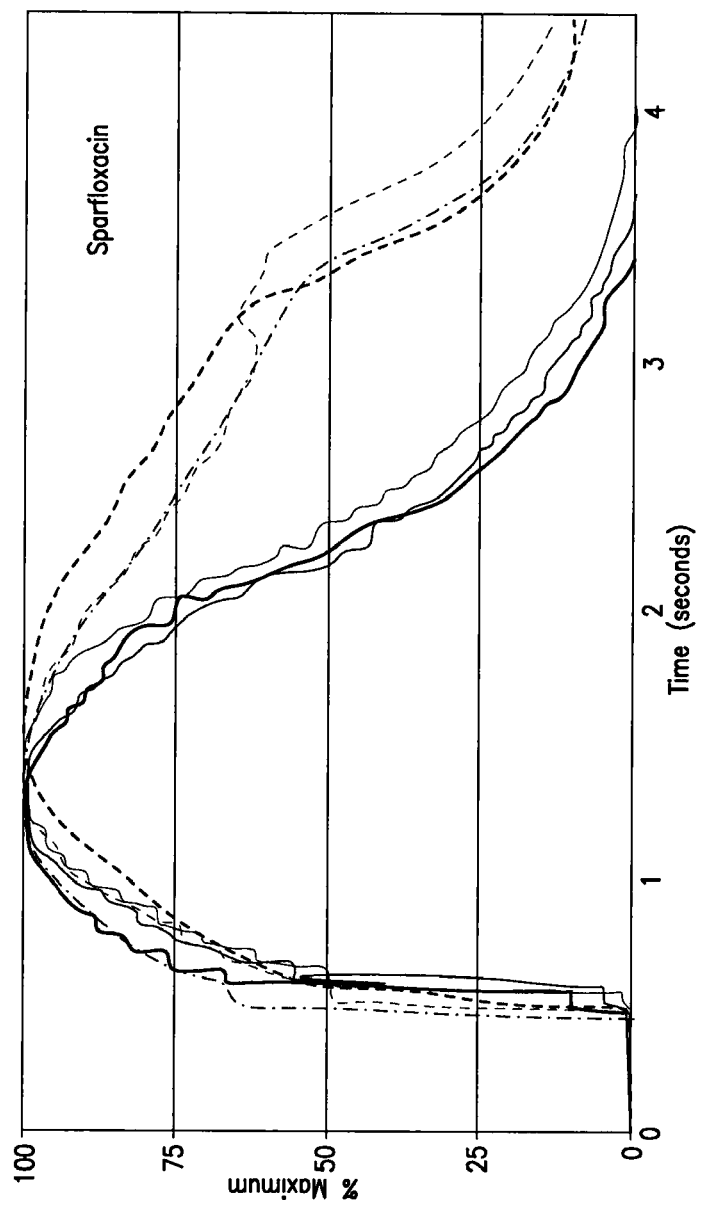
FIG. 5 is a graphical representation of calcium transient in NRVMs treated with A) sparfloxacin; and B) cisapride. The continuous lines being are refer to the control and the dashed lines refer to the drug treated NRVMs.
Figure 5B:
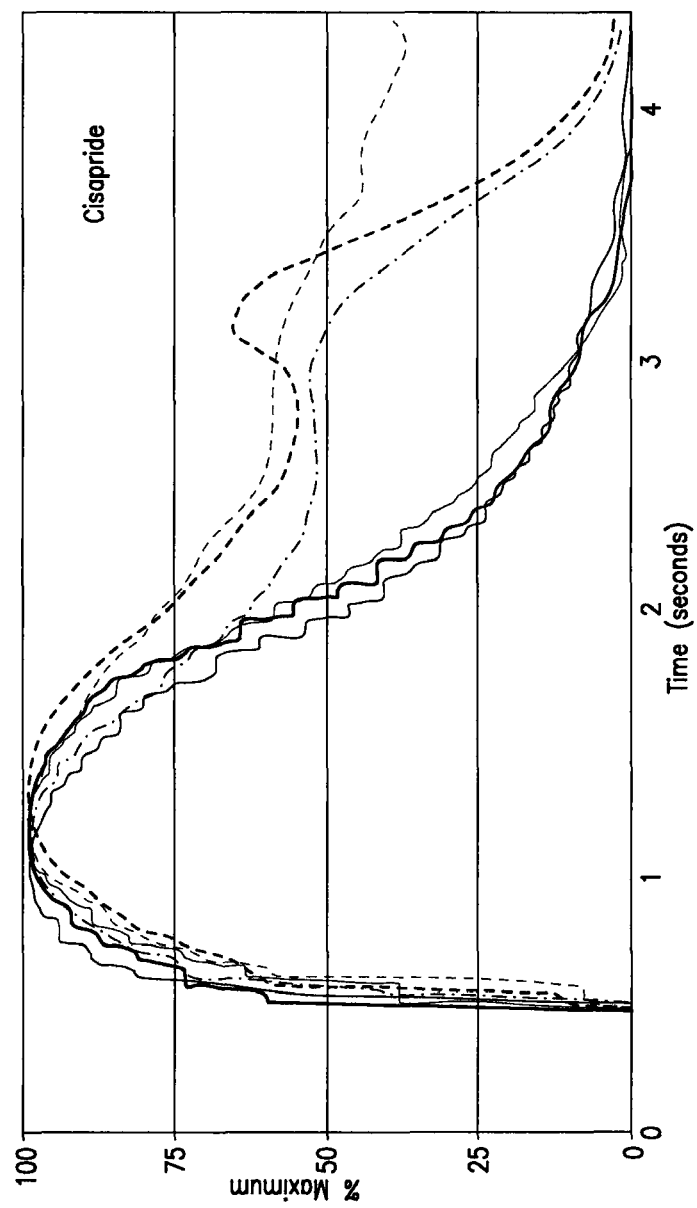

FIGS. 5A and 5B show calcium transient in drug treated NRVMs. NRVMs are treated with 100 µM sparfloxacin (FIG. 5A) and 1 µM cisapride (FIG. 5B), two drugs already known to induce arrhythmia. Cells are stimulated with a single pulse current and with the compounds present in the buffer used during the recording. The average signals from three control wells (continuous line) and three compound treated wells (dotted line) are shown.

In another set of experiments NRVMs that have been stimulated multiple times at a frequency of 2 Hertz showed impaired response in presence of arrhytmogenic drugs (FIGS. 6A and 6B). FIGS. 6A and 6B show exemplary single cell recordings of continuous stimulation in NRVMs. NRVMs are treated for 3 days with thyroid hormone and stimulated with a 2 Hz electrical current. The percentage of the maximum intensity of calcium transient, recorded for single cells from a control and a sparfloxacin treated samples are showed. Cells treated with drug respond to stimulation with irregular calcium flux.

Figure 7:
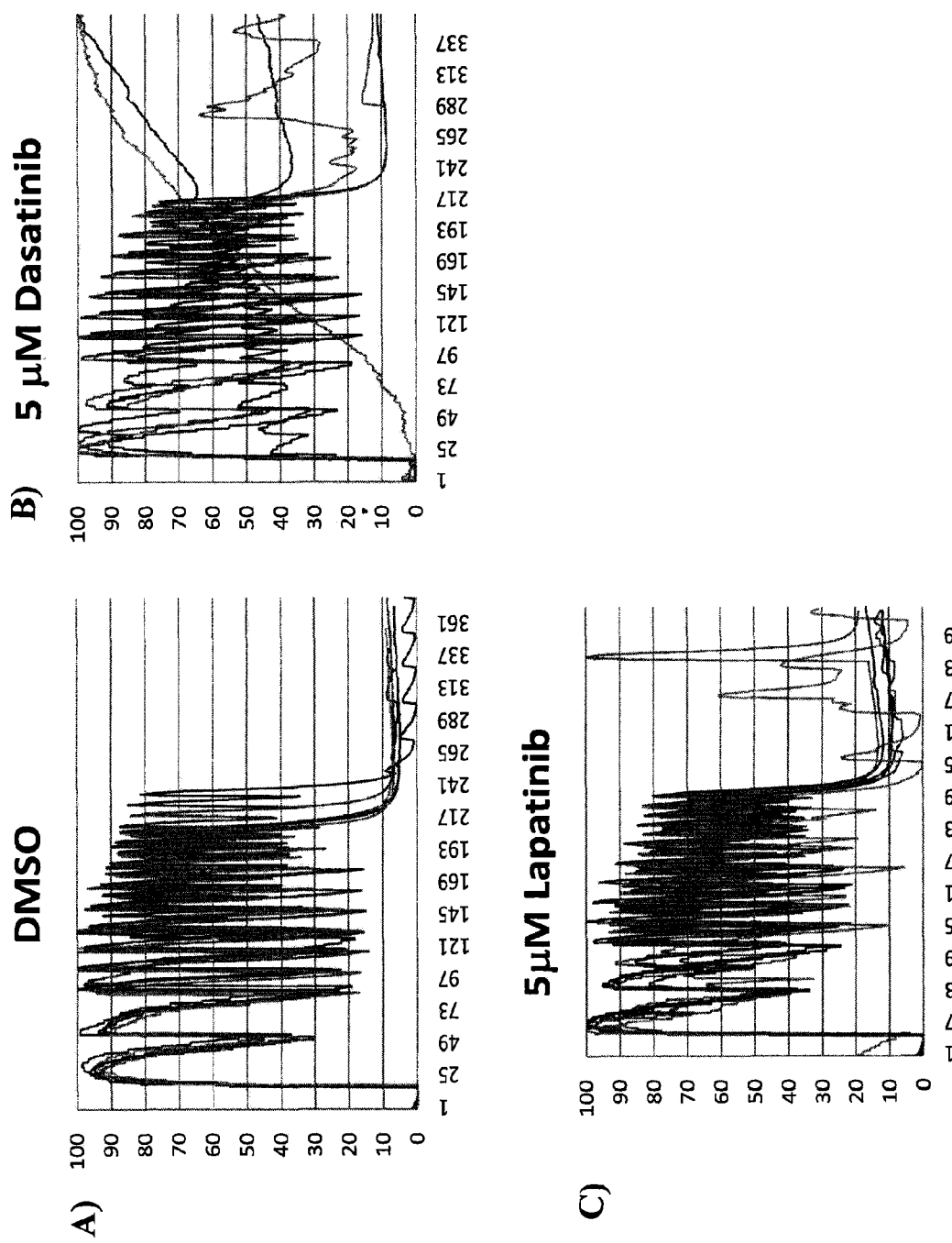
FIG. 7 is a graphical representation of cell recordings of NMRVs assayed with: A) DMSO; B) Dasatinib; and C) Lapatinib.

The CTIC has been tested on tyrosine kinase inhibitors with different cardiotoxicity, confirming the value of automatic calcium flux measurements for toxicity screening. Dasatinib (Sprycel) is an ATP competitive Abl-kinase inhibitor with documented cardiotoxicity while Lapatinib (Tykerb) is an ERBB2 (EGF receptor 2) inhibitor with lower toxicity. When NRVCs are treated with the 2 compounds and stimulated at 2 Hz, they show impaired calcium response in presence of Dasatinib while only subtle differences with Lapatinib (FIG. 7). FIG. 7 shows assays of kinase inhibitors with different toxicity on NRVMs. NRVMs (6 replicates) are treated with 5 µM Dasatinib (center) or Lapatinib (right), two tyrosine kinase inhibitors and stimulated with 2 Hz frequency. Calcium flux (fluo-4 fluorescence) is automatically acquired with the CTIC. The recordings point out the irregularity of calcium flux in samples treated with Dasatinib compared to Lapatinib and control (DMSO).

The calcium analysis has been applied also to hESC-derived cardiomyocytes. One of the hES cell lines expresses the puromycin resistance gene under the control of the cardiac specific promoter for the α isoform of the Myosin Heavy Chain (αMHC). The cassette allows the isolation of beating cardiospheres composed almost entirely of cardiomyocytes after the differentiation of the stem cells and few cycles of drug selection.

Figure 8:
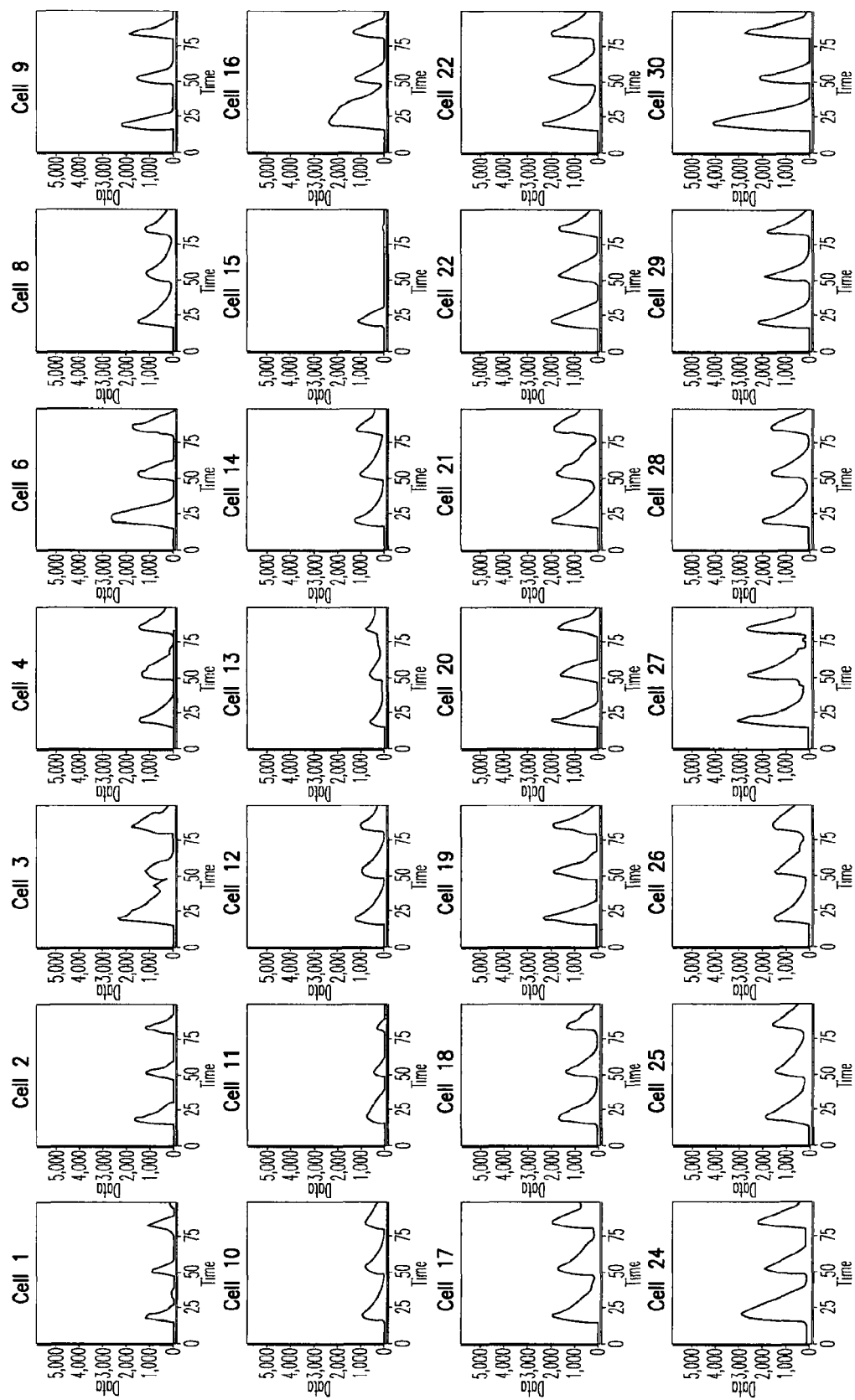
FIG. 8 graphically depicts the calcium traces of several different human embryonic stem cell (hESC)-derived cardiomyocytes responding to stimulation.

In this experiment, the selected cardiospheres are dissociated and plated on glass bottom 96-well dishes. This procedure allows the formation of monolayer of cells with a percentage of cardiomyocytes variables between 70 and 90%. After loading with fluo-4 and Hoechst 33342 the cells are stimulated 3 times with at 1 Hz frequency using the CTIC instrument. Dapi and α-Actinin staining of a representative well show that at least 80% of the cells are represented by cardiomyocytes. The Calcium Analysis Software is able to segment the cells despite the high cellular density and measured the calcium transient for tens of responding cells. The large majority of the responders show three isolated transients, synchronized with the stimuli that were furnished by the instrument. FIG. 8 shows calcium traces for several cardiomyocyte cells responding to the stimulation that are analyzed by the software.

Taken together these experiments demonstrate the ability of the automated CTIC to record intracellular calcium flux in cardiac cells of different origin. The ability to identify alterations in membrane conductance or calcium handling validates the use of the CTIC as a screening tool for compounds that interfere with cardiac physiology. The instrument has an open architecture that allows the introduction of new modules and filter to measure parameters emitted by other fluorescent probes. Furthermore, the Calcium Analysis Plug-in Software is not necessarily bound to images acquired with the CTIC, but can analyze any cellular transient that is measured by variations in fluorescence intensity, thus making the software a standalone product that expand the capacity of the CyteSeer™ high content analysis software.

EXAMPLE 2

Induction of Action Potentials Using ChR2 and NRVMs

To evaluate if the ChR2 is an effective instrument to induce action potentials, experiments are conducted using NRVMs as a source of homogeneous cardiac cells. Despite the fact that the most direct way to produce light-induced cardiac action potential would be the expression of ChR2 directly in cardiac cells, it is likely an approach unsuitable for physiological studies, mainly because ChR2 is highly permeable to several monovalent and divalent cations ($Ca^{2+}$, $Na^+$ and $K^+$) that are fundamental in the genesis of the action potential.

The goal of the present invention is to trigger only the action potential without affecting the conductibility of the cardiac membrane. Furthermore, introducing the ChR2 gene in primary cardiac cells would increase the complexity of the procedure for cells isolation. Thus, the approach followed is to express ChR2 in another cell system, easier to culture and modify, that will be coupled to cardiomyocytes. To that end, for the present experiment, expression of ChR2 in HeLa cells is performed, a cervical cancer derived cell lines routinely used in research laboratories. To facilitate the propagation of the depolarization to cardiomyocytes connexin 43 (Cx43) can also be expressed together with ChR2.

In a first set of experiments the possibility to express ChR2 and Cx43 together in HeLa cells and the ability of Cx43 to form gap junction with cardiomyocytes is evaluated. NRVMs are seeded on 96-well dishes and HeLa cells seeded on top of them the day after, 24 hours after been transfected with the empty vectors or plasmids carrying ChR2 and Cx43. Confocal immunofluorescence analysis of the cells 24 hours after coculture is performed. The images clearly demonstrate the expression and mainly membrane localization of ChR2 in HeLa as well as the formation of gap junctions between HeLa cells expressing Cx43 and the adjacent cardiomyocytes. Specifically, NRVMs and HeLa transfected with the empty vectors or with plasmids expressing ChR2 and Cx43 are co-cultured, fixed and stained for nuclei, a specific ventricular cardiac marker (MLC2v) and ChR2 or Cx43 and compared. Confocal Imaging showed the ability of ChR2 to be expressed in HeLa and the formation of gap junction between HeLa expressing Cx43 and adjacent cardiomyocytes.

The same samples are analyzed for light-induced action potential and calcium transients. Movies are recorded during the illumination of the samples with a FITC filter setting. Because the excitation peak of fluo-4, the fluorophore used to measure intracellular calcium, and ChR2 opening are basically the same (460 nm), the same FITC filter set is used to induce and acquire the calcium transient. In a typical experiment, cells are loaded with fluo-4, bathed in tyrodes solution and 30 ms exposition/frame movies were acquired with a Hamamatsu ORCA-ER™ camera mounted on a Leica DMI 4000B™ inverted microscope. In order to acquire the exact instant when the action potential is induced, the recordings are started with the shutter closed and successively manually opened.

Several key frames of movies are acquired with a 20× and 5× objectives. Frames showing the light-induced calcium transient acquired with a 20× objective are taken. The responding cardiomyocytes appeared brighter at the peak of the transient. Images acquired with a 5× objective show that the depolarization started from the bottom left of the field and propagated to the other cells. Immunofluorescence for nuclei and the ventricular cardiomyocytes marker MLC2v show that the field is covered mainly by HeLa cells while the cardiomyocytes form an intricate reticulum.

For the 20× movie, a first frame is acquired after the shutter opening, when the calcium transient has not begun yet and the intracellular calcium concentration is low. Later frames show the pick of the transient, with the cardiomyocytes responding synchronously while later frames show the down stroke phase of the transient. Subsequent frames then show the cells just before the plateau, when the fluo-4 signal is almost at the same level as at the beginning. The same results are obtained with the 5× objective, with the only difference that instead of being synchronized the depolarization started on the bottom left of the field and then it propagates to the right.

It is likely that the depolarization is triggered by few cells and then propagates to the adjacent cardiomyocytes. This conclusion comes from two observations: (a) only few of the transfected HeLa cells express ChR2 and Cx43, and (b) in the coculture the NRVMs form an intricate reticulum and are connected by gap junctions. When transfected with the empty vectors no light-induced massive calcium transient is observed, but just few unsynchronized transients involving few cells at a time. Another observation that points out the utility and power of the system is the fact that after the first transient, under constant illumination, the cells are refractory to new depolarization. After the closing of the shutter though, the cells are ready to respond again. This is likely explained by the fast refractory status that achieves ChR2 soon after illumination. Closing the shutter and blocking the light source reactivates ChR2 and allows a new stimulation.

Taken together these experiments with ChR2 validate the concept of using indirect ChR2 expression to induce light-triggered cardiac depolarization. The experiments have also demonstrated few keys properties of the system that likely will allow the development of a flexible and robust system. First, the indirect excitation is fundamental to physiological tests in cardiomyocytes and can be adapted to a variety of cardiac cells. Secondly, the refractory period of ChR2 allows a single stimulation under continuous state. Third, the rapid return of ChR2 to a sensitive state will allow the stimulation of cardiomyocytes with a constant frequency. It is estimated that 2-4 Hz stimulation can easily be tolerated by the system just opening and closing the shutter. Lastly, the system works with different objectives, allowing accurate measurements under high magnification (20×) but also measurements of the conduction velocity in larger fields of view, using objectives with lower magnification (5×).

EXAMPLE 3

Analysis of ChR2/Cx43 Contribution to Light-Inducted Action Potential Generation and Propagation in Different Cell Lines The previous examples suggest both Cx43 and ChR2 are expressed at high level only in a low number of transfected HeLa; however the levels are sufficient to allow light-induced action potential in NRVMs. Further experiments may be performed to clarify the role of Cx43 in propagating the action potential to nearby cardiomyocytes and the amount of ChR2 necessary to induce the depolarization. The use of various cell lines may also be explored to determine cell lines exhibiting the highest efficiency (i.e., more cell expressing the exogenous proteins) but also to determine cell lines that exhibit various patterns between cardiomyocytes and ChR2 expressing cells. Three methods may be utilized to make such determinations.

First, evaluation of different cell lines for light-induced triggering of action potential may be performed. Different cell lines may be analyzed for the ability to induce light-triggered action potential in cardiomyocytes. Cells may be transfected with the same amount of plasmids carrying ChR2 and Cx43 that have been used in the previous examples (e.g., 0.2 µg ChR2+0.2 µg Cx43 for each well of a 6-well dish with Lipofectamine™ 2000 from Invitrogen) and, after 24 hours, may be seeded on top of NRVMs in a 96-well glass bottom plate. The day after cells are loaded with fluo-4 and analyzed for light-induced action potential under an inverted fluorescence microscope. After light stimulation the cells are fixed and analyzed for ChR2 and Cx43 expression. Example of cells that may be utilized are carcinoma derived HeLa, NIH/3T3 fibroblasts and embryonic kidney HEK293. Additionally, cell lines or primary cells that retain the ability to adhere to specific molecules may be analyzed. Such cells are expected to be significant to determine the effect of different patterning strategies for measuring the velocity of conduction. One example can be represented by the Human Umbilical Vein Endothelial Cells HUVEC, which can adhere to vitronectin.

Second, evaluation of different ratios of ChR2:Cx43 may be performed for analysis of action potential induction/propagation. To light-trigger the action potential to cardiomyocytes two conditions need to be satisfied: the cellular membrane in the ChR2 expressing cells need to be depolarized by the opening of the channel and the depolarization must be propagated to the nearby cardiomyocytes reaching the threshold level necessary to induce the action potential. While the ChR2 is the protein responsible for the light-induced membrane depolarization, expressed of Cx43 facilitates the propagation of depolarization to nearby cells. To evaluate Cx43 in this latter event various cell lines may be transfected with different ratios of ChR2:Cx43 plasmids (e.g., 0.4 µg ChR2+0.05 µg Cx43; 0.35 µg ChR2+0.05 µg Cx43; 0.3 µg ChR2+0.1 µg Cx43; 0.3 µg ChR2+0.4 µg Cx43) and subsequently analyzed for light-induced action potential as discussed above. Cells may also be analyzed for protein expression by immunofluorescence and western blot.

Third, evaluation of intensity versus diffusion may be performed for analysis of triggering the action potential. As shown in previous examples, high expression levels for ChR2 and Cx43 appears only in a minority of cells. The mechanism responsible for the action potential generation and propagation is to be evaluated. The two hypothetic explanations are: (a) the ChR2 expression is necessary only for a small population of cells that will be in contact with NRVMs; or (b) a low (and so undetectable) but diffused expression of ChR2 is required. To solve this dilemma, different experiments are conducted in parallel: an immortalized cell line may be transfected with increasing amounts of ChR2 and Cx43 plasmid DNA. Carrier DNA is added to maintain constant the amount of total DNA transfected and cells seeded on top of NRVMs. Simultaneously, another sample of cells is transfected with a higher amount of ChR2 and Cx43 DNA and mixed with untransfected cells at different ratios (ranging from 1:1 to 1:100) before seeding them on NRVMs. One day after seeding, the cells are analyzed for light-triggered action potential as in the previous examples. If the prevailing mechanism is the necessity of expression of ChR2 only in few transfected cells, small or no difference is expected between the two groups of transfected cells. If the expression should be present (even at low level) in the large majority of cells, the present invention provides that a larger reduction of the efficiency in the samples that are diluted with untransfected cells will be observed. Immunofluorescence and/or western blot analysis can be performed to link the results to the level of protein expression and diffusion.

EXAMPLE 4

Generation of Stable Cell Lines Expressing ChR2 and/or Cx43

To increase the efficiency of light-induced action potential in cardiomyocytes and to allow coculturing of trigger cells and cardiomyocytes for longer periods development of cell lines constitutively expressing ChR2 and Cx43 may be performed. This is accomplished by isolating clones expressing both ChR2 and Cx43 after standard DNA transfection/selection methodology. Additionally, an inducible promoter (e.g. tet-off system from Clontech) or lentiviral system may be utilized.

Generation of stable clones with the plasmid DNA transfection/selection methodology may be performed as follows. Cell may be transfected with a plasmid DNA carrying the ChR2 gene under control of a constitutive promoter and also expressing a gene that confers drug resistance. A plasmid including the Neo resistance gene may be utilized. Cells are transfected with a standard lipid method (e.g., Lipofectamine™ 2000, Invitrogen) and seeded at low density in 15 cm cell culture dishes. The day after G418 is added to medium and changed every 2 days. The optimal concentration that kills the untransfected cells in a period of 4-6 days is determined empirically and used during clone generation. After 7-10 days from the starting of the selection, clones that are derived from a single cell are expected to present in the dishes. The clones are manually isolated with a pipette and transferred to 96-well plates to be cultured under selection. The isolated clones may be successively expanded to bigger dishes and analyzed for ChR2 expression by western blot and/or immunofluorescence. Clones expressing higher level of ChR2 are then amplified and frozen in a large number of vials. In a second phase, few clones are transfected and selected against a second plasmid constitutively expressing Cx43 and a different selection (e.g., puromycin). The new clones are the analyzed for expression of both ChR2 and Cx43 and few of them tested for light-induced action potential induction in NRVMs.

Generation of stable clones expressing inducible proteins may be performed as follows. An inducible promoter system, for example the tet-off inducible system from Clontech is used to obtain the expression of the protein. The tet-off system relies on the expression of a tetracycline regulated repressor/promoter to repress the expression of the gene of interest in presence of tetracycline. The removal of tetracycline from the medium inactivates the repressor and the gene is turned on. The tet off system allows the expression of the toxic protein only after coculturing the cells with NRVMs. The tet-off system may be used to prevent the introduction of tetracycline in the medium during the assay. Tetracycline and anthracyclines are well known to bind calcium and interfering with calcium handling in the heart. The plasmid carrying the gene (ChR2 or Cx43) is transfected in a cell line constitutively expressing the tet-off protein (e.g., CHO, PC12 MEF/3T3). Selection and clone isolation is then performed as discussed above but in presence of tetracycline or doxycycline in the medium. After removal of the antibiotic the clones are analyzed for the expression of the protein of interest by immunofluorescence and/or western blot. Once the right clones are identified they are transfected and selected for expressing the other protein using the protocol described above.

As an alternative expression of ChR2 and Cx43 may be by retroviral transduction. As a third strategy to express ChR2 and Cx43 in cells lentivirus is utilized. The virus may be produced purified and concentrated and utilized to infect cells at different multiplicity of infection. The day after the infection the cells are detached and seeded in 96-well dishes at a density of one cell per well or less to originate clones that will express the protein of interest. Clones are then tested for expression of the protein by immunofluorescence or western blot. The lentivirus may be utilized also to infect primary or hard to transfect cells.

EXAMPLE 5

Validation of Light-Induced Action Potential to Test Cardiotoxicity

Light-induced action potential may be validated on NRVMs against compounds already known to bind ion channel and with documented cardiotoxicity. The results are then compared with those ones obtained by electrical stimulation.

Acquisition and analysis of light-induced calcium transient. Cells, transiently or constitutively expressing ChR2 and Cx43, are seeded on top of NRVMs in 96-well glass bottom plates and after 24 hours loaded with fluo-4 and Hoechst 33342 to be analyzed. Cells are then light-stimulated and fluorescence simultaneously acquired under the CTICs without electrical stimulation, using filter sets optimized for fluo-4 and the nuclear dye Hoechst. The instrument will focus automatically on the nuclear channel and acquire a single image of nuclei a short movie (3-6 sec.) of the fluo-4 channel. For comparison few wells, containing both NRVMs and ChR2 expressing cells or only NRVMs, will be electrically stimulated and acquired with the same instrument. The software developed to analyze calcium transients may be utilized to obtain a curve of calcium flux and to extrapolate values like the FWHM.

The ultimate goal of this method is to demonstrate analyzing calcium flux using light-induce trigger and to identify differences between electrical and optical stimulation Testing the effect of cardiotoxic drugs. The ability of the assay to discriminate the effect of drugs that affect action potential and calcium release in cardiomyocytes is conducted with drugs well known to be cardiotoxic. The validation relies on a limited number of concentrations and replicates. Examples of pro-arrhythmic drugs that bind the hERG K$^+$ channel and that may be utilized to validate the assay are the parasympathomimetic Cisapride, the fluoroquinolone antibiotic Sparfloxacin and the antihistamine Astemizole. All have been removed from the market or are accompanied by severe black-box labels. High-potency hERG blockers (e.g., lidoflazine, terfebadine and haloperidol IC$_{50}$<0.1 µM) may be compared to moderate blockers (e.g., sertindole, thioridazine and prenylamine 0.1 µM<IC$_{50}$<1 µM), low blockers (e.g. propafenone, loratadine, pyrilamine, lovastatin and chlorpheniramine IC$_{50}$>1 µM) and ineffective blockers (e.g. cimetidine, pentamidine and arsenic trioxide IC$_{50}$>300 µM).

Furthermore, several Class I anti-arrhythmic drugs that bind the Na$^+$ channels and reduce the depolarizing current can be also tested to measure the effect on Ca$^{2+}$ release. These drugs are Lidocaine, Quinidine, Disopyramide and Tocainide. Drugs that directly affect calcium release and uptake in the ER may also be tested. Examples are the SERCA2 inhibitor Thapsigargin, the L-type calcium channel blocker Verapamil and the positive inotropic drugs Epinephrine and Digoxin. The concentration range during testing may be varied with their IC$_{50}$ of the compounds and with the data available in literature, but generally they are in the range of 10 nM to 100 µM. The data may be compared between the light-induced and electrical stimulation experiments and also with data present in the literature.

ChR2 and Cx43 expressing cells are seeded on top of NRVMs and analyzed as described above. The drugs are added directly in the tyrodes solution, before the recording, for channel blockers, or in the medium during 2-3 days of culturing for drugs that have longer effects.

EXAMPLE 6

Validation of Light-Induced Action Potential to Measure Velocity of Conduction

Figure 9:
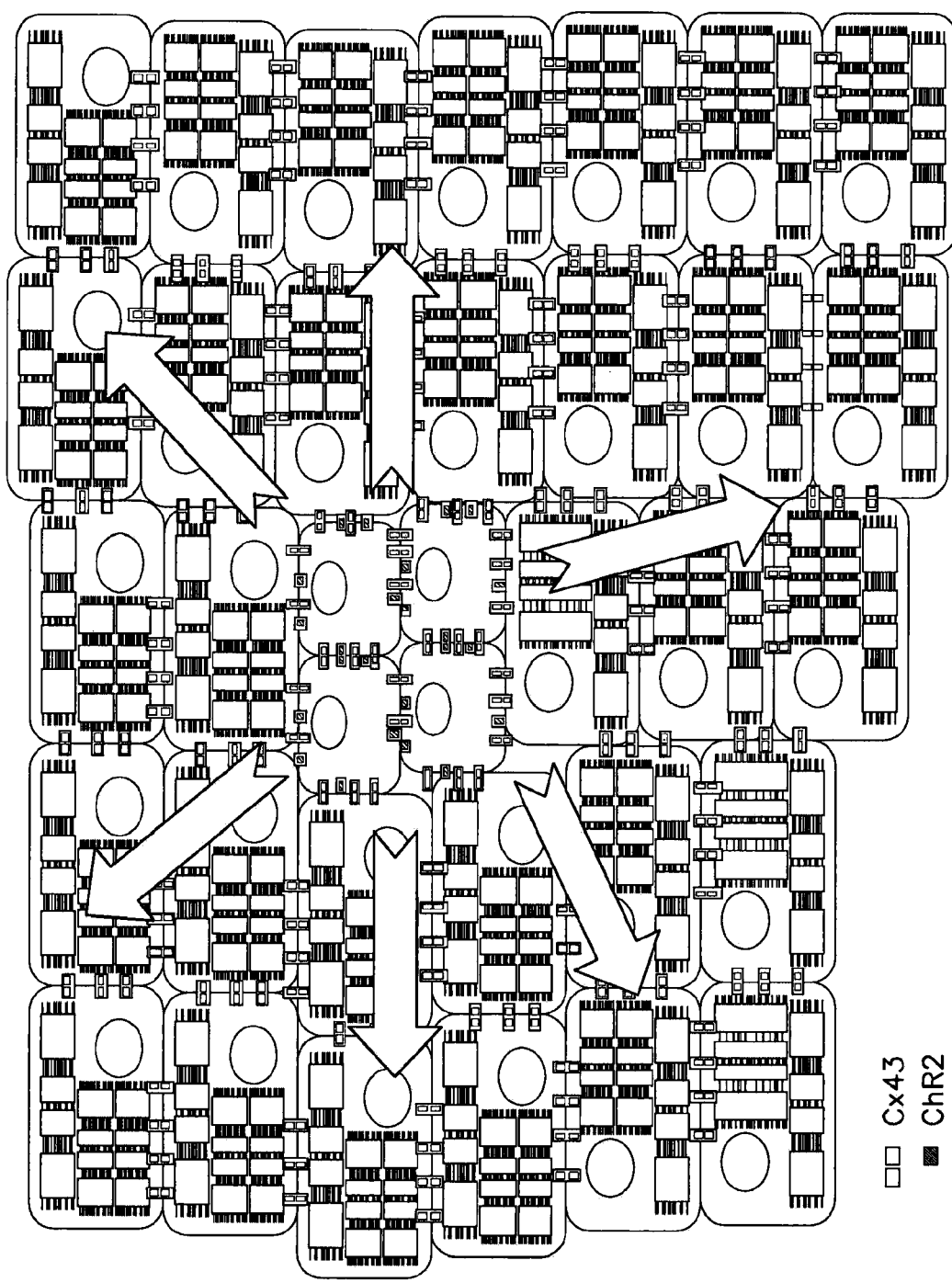
FIG. 9 is a pictorial schematic of seeding of ChR2 expressing cells and NRNMs for measuring velocity of conduction.

To measure the velocity of propagation we will develop a system where ChR2 expressing cells are localized in a specific region of the field of view and surrounded by NRVMs. The light will depolarize this region and the action potential will be induced in the surrounding cardiomyocytes propagating to the other cells in a radial direction, as schematized in FIG. 9. As shown in FIG. 9, ChR2 expressing cells are seeded in a small spot on the dish and let to adhere. After few hours the dish is washed and NRVMs plated and let to adhere in the region free of the previously seeded cells. Light induced action potential is recorded propagating from the central spot to the periphery. Fluo-4 fluorescence will be acquired and algorithms developed to measure the velocity of conduction.

Light triggered analysis of velocity of conduction may be performed as follows. Cells transiently or constitutively expressing ChR2 and Cx43 are seeded on matrigel coated dishes or plates. The cells, in one small drop (0.1 to 2 µl), are placed in the central region of the dish and let adhere for few hours in a cell culture incubator. Different concentration of cells, length of deposition and volume of the drop will be tested to give a confluent spot in the region where the cells were deposited. After few hours, necessary to let the cell adhere and form a confluent region the dish will be extensively washed to remove the unattached cells. NRVMs are seeded on the same dish to attach in the cell-free zone. After 1-2 days of coculture, necessary for the cardiomyocytes to mature and to form abundant gap junctions, cells are loaded with fluo-4 and Hoechst 33342 and analyzed under a fluorescence inverted microscope. An image of the nuclear channel is acquired and subsequently movies (30 Hz or higher) acquired of the fluo-4 channel. The images are acquired in a way that the ChR2 expressing cells are located in the center or along the border of the field, depending by the size of the objective that is used and by the radius of the region where these cells are located. The shutter is manually turned on and off during the recording to trigger the action potential. Objectives ranging from 5× to 20× may be tested to acquire regions of different extension. An algorithm to measure the velocity of conduction may be used. The velocity of conduction may be expressed as pixel/second or um/second.

Assay validation with compounds that affect velocity of conduction may be performed as follows. The assay for measuring velocity of conduction in cardiomyocytes may be validated with compounds that are known to affect the velocity of conduction. Examples of such compounds are Quinidine, a class IA antiarrhythmic agent that blocks the fast Na inward current; the class IC antiarrhythmic drug Propafenone™, the gap junction uncoupler 1-Heptanol, and gap junction modulator Rotigaptide/ZP123. Concentrations should be similar to those utilized in literature to test the effects of these compounds (e.g., 10 µM to 200 µM for Quinidine, 0.1 to 1 mmol/L 1-Heptanol and 1 nm to 10 µM for ZP123). The experiment may be conducted as discussed above, but the compounds are added to tyrodes solution beating the cells few minutes before stimulation/acquiring the calcium transient. The velocity of conduction is measured with the same algorithm discussed above and results compared between controls and treatments.

Although the invention has been described with reference to the above example, it will be understood that modifications and variations are encompassed within the spirit and scope of the invention. Accordingly, the invention is limited only by the following claims.

What is claimed is:
1. A method of screening a drug candidate for cardiotoxicity comprising:
  (a) providing a cocultured sample, comprising:
    (i) at least one cardiomyocyte cell, and
    (ii) at least one non-cardiomyocyte cell selected from the group consisting of a HeLa cell, a CHO cell and NIH/3T3 cell, wherein the at least one non-cardiomyocyte cell contains a heterologous nucleic acid encoding Channelrhodopsin1 (ChR1) or Channelrhodopsin2 (ChR2) light sensitive protein in addition to a heterologous nucleic acid encoding a connexin protein selected from the group consisting of Cx23, Cx25, Cx26, Cx29, Cx30, Cx30.2, Cx30.3, Cx31, Cx31.1, Cx31.9, Cx32, Cx33, Cx36, Cx37, Cx39, Cx40, Cx40.1, Cx42, Cx45, Cx46, Cx47, Cx50, Cx59, Cx62, or a combination thereof;
  (b) contacting the sample of (a) with a drug candidate;
  (c) optically activating the light sensitive protein in the at least one non-cardiomyocyte cell to induce an action potential in the at least one cardiomyocyte cell and produce an efflux of calcium cations from the non- cardiomyocyte cell thereby optically inducing cardiomyocyte contraction with the at least one non-cardiomyocyte cell; and (d) measuring an effect of the efflux of cations on the cardiomyocyte, thereby identifying the drug candidate as cardiotoxic, wherein the method does not use an electric current to stimulate contraction of the at least one cardiomyocyte cell.

2. The method of claim 1, wherein the non-cardiomyocyte cell is a HeLa cell.

3. The method of claim 1, wherein the cardiomyocyte and non-cardiomyocyte cell are connected via a plurality of gap junctions, and arranged as a monolayer.

4. The method of claim 1, wherein the sample is cocultured for at least 1, 2, 3, 4, or 5 days before contacting the sample with the drug candidate.

5. The method of claim 1, wherein the heterologous nucleic acid further comprises an inducible promoter.

6. The method of claim 1, wherein the non-cardiomyocyte cell is stably transformed with the heterologous nucleotide.

7. The method of claim 1, wherein, the ratio of cardiomyocyte to non-cardiomyocyte cells is greater than about 1:1, 2:1, 3:1, 4:1, 5:1, 10:1, 50:1, 100:1, 500:1 or 1000:1.

8. The method of claim 1, wherein the effect is selected from the group consisting of cardiomyocyte action potential, cardiomyocyte intracellular calcium level, velocity of conduction, or a combination thereof.

9. The method of claim 8, wherein the effect is cardiomyocyte action potential or velocity of conduction.

* * * * *

UNITED STATES PATENT AND TRADEMARK OFFICE
CERTIFICATE OF CORRECTION

PATENT NO. : 10,001,470 B2
APPLICATION NO. : 12/960313
DATED : June 19, 2018
INVENTOR(S) : Mark Mercola et al.

It is certified that error appears in the above-identified patent and that said Letters Patent is hereby corrected as shown below:

In the Specification

In Column 1, Lines 15 through 19, please replace:
"This invention was made with government support under NIH/NHLBI Grant No. R42HL086076-01 awarded by the National Institutes of Health/National Heart, Lung, and Blood Institute. The government has certain rights in the invention."

With:
"This invention was made with government support under HL086076 awarded by the National Institutes of Health. The government has certain rights in the invention."

Signed and Sealed this
Third Day of March, 2020

Andrei Iancu
*Director of the United States Patent and Trademark Office*